US005994292A

United States Patent [19]
Tosato et al.

[11] Patent Number: 5,994,292
[45] Date of Patent: Nov. 30, 1999

[54] INTERFERON-INDUCIBLE PROTEIN 10 IS A POTENT INHIBITOR OF ANGIOGENESIS

[75] Inventors: Giovanna Tosato, Bethesda, Md.; Anne L. Angiolillo, Washington, D.C.; Cecilia Sgadari, Bethesda, Md.

[73] Assignee: The United States of America as represented by the Department of Health and Human Services, Washington, D.C.

[21] Appl. No.: 08/455,079

[22] Filed: May 31, 1995

[51] Int. Cl.$^6$ .................................................. A61K 38/00
[52] U.S. Cl. .................................... 514/2; 514/4; 514/12; 514/21; 530/300; 530/324; 530/325; 530/326; 530/327; 530/328
[58] Field of Search ............................. 514/12, 21, 214, 514/2, 4; 530/324, 300, 325, 326, 327, 328; 424/85.7, 85.2, 85.1

[56] References Cited

U.S. PATENT DOCUMENTS

| | | | |
|---|---|---|---|
| 5,086,164 | 2/1992 | Maione et al. | 530/324 |
| 5,112,946 | 5/1992 | Maione et al. | 530/324 |
| 5,346,686 | 9/1994 | Lyle et al. | 424/1.41 |
| 5,474,981 | 12/1995 | Leder et al. | 514/2 |
| 5,728,377 | 3/1998 | Sarris et al. | 530/351 |

FOREIGN PATENT DOCUMENTS

| | | |
|---|---|---|
| 0 589 719 A1 | 3/1994 | European Pat. Off. . |
| WO 88/05783 | 8/1988 | WIPO . |
| WO 90/08824 | 8/1990 | WIPO . |
| WO 94/04670 | 3/1994 | WIPO . |
| WO 94/13321 | 6/1994 | WIPO . |
| WO 94/21277 | 9/1994 | WIPO . |
| WO 97/00691 | 1/1997 | WIPO . |

OTHER PUBLICATIONS

Angiolillo et al, Human Interferon–inducible Protein 10 is a Potent Inhibitor of Angiogenesis In Vivo, *The Journal of Experimental Medicine* vol. 182, pp. 155–162, Jul. 1995.

Strieter et al, Interferon γ–Inducible Protein 10 (IP–10), a Member of the C–X–C Chemokine Family, is an Inhibitor of Angiogenesis, *Biochemical and Biophysical Research Communications*, vol. 210, No. 1, pp. 51–57, May 5, 1995.

Ohmori et al, IFN–γ Selectively Inhbits Lipopolysaccharide–Inducible JE/Monocyte Chemoattractant Protein–1 and KC/BRO/Melanoma Growth–Stimulating Activity Gene Expression in Mouse Peritoneal Macrophages, *The Journal of Immunology*, vol. 153, No. 5, pp. 2204–2212, Sep. 1, 1994.

Bedard et al, Cytokine–Induced Expression of mRNAs for Chemotactic Factors in Human Synovial Cells and Fibroblasts, *Journal of Cellular Physiology*, vol. 154, No. 2, pp. 433–441, Feb. 1993.

Luster et al, Interferon–inducible gene maps to a chromosomal band associated with a (4;11) translocation in acute leukemia cells, *Proc. Natl. Acad. Sci. USA*, vol. 84, pp. 2868–2871, May 1987.

Presta et al, New Aspects of Blood Vessel Growth: Tumor and Tissue–Derived Angiogenesis Factors, *Haemostasis* 18:6–17 (1988).

Folkman et al, Angiogenic Factors, *Science*, vol. 235, pp. 442–447, Jan. 23, 1987.

Gupta et al, Inhibition of Endothelial Cell Proliferation by Platelet Factor–4 Involves a Unique Action on S Phase Progression, *The Journal of Cell Biology*, vol. 127, No. 4, pp. 1121–1127, Nov. 1994.

Luster et al, Genomic Characteriztion of a Gamma–Interferon–Inducible Gene (IP–10) and Identification of an Interferon–Inducible Hypersensitive Site, *Molecular and Cellular Biology*, vol. 7, No. 10, pp. 3723–3731, Oct. 1987.

Sarris et al, Human Interferon–inducible Protein 10: Expression and Purification of Recombinant Protein Demonstrate Inhibition of Early Human Hematopoietic Progenitors, *J. Exp. Med.*, vol. 178, pp. 1127–1132, Sep. 1993.

Maione et al, Inhibition of Angiogenesis by Recombinant Human Platelet Factor–4 and Related Peptides, *Science*, vol.247, pp. 77–79, Jan. 5, 1990.

D'Amore, Antiangiogenesis as a Strategy for Antimetastasis, *Seminars in Thrombosis and Hemostasis*, vol. 14, No. 1, pp. 73–78, 1988.

Luster et al, IP–10, a –C–X–C– Chemokine, Elicits a Potent Thymus–dependent Antitumor Response In Vivo, *J. Exp. Med.*, vol. 178, pp. 1057–1065, Sep. 1993.

Luster et al, γ–Interferon Transcriptionally Regulates an Early–Response Gene Containing Homology to Platelet Proteins, *Nature*, vol. 315, pp. 672–676, Jun. 20, 1985.

Battegay, "Angiogenesis: Mechanistic Isusights" (1995), Biosis Abstract # 95:443403.

O'Reilly, "Angiostatin" (1994), Biosis Abstract #94:549066.

*Primary Examiner*—Cecilia J. Tsang
*Assistant Examiner*—Patrick R. Delaney
*Attorney, Agent, or Firm*—Morgan & Finnegan, L.L.P.

[57] ABSTRACT

The present invention is interferon-inducible protein 10 and fragments and analogs of interferon-inducible protein 10 as inhibitors of angiogenesis. The present invention is also the use of interferon-inducible protein 10 (IP-10) as well as fragments and analogs of IP-10 as potent inhibitors of angiogenesis. IP-10 profoundly inhibited basic fibroblast growth factor (bFGF)-induced neovascularization in immunocompromised mammals. In addition, IP-10, is useful in a dose-dependent fashion in suppressing endothelial cell differentiation into tubular capillary structures.

35 Claims, 10 Drawing Sheets

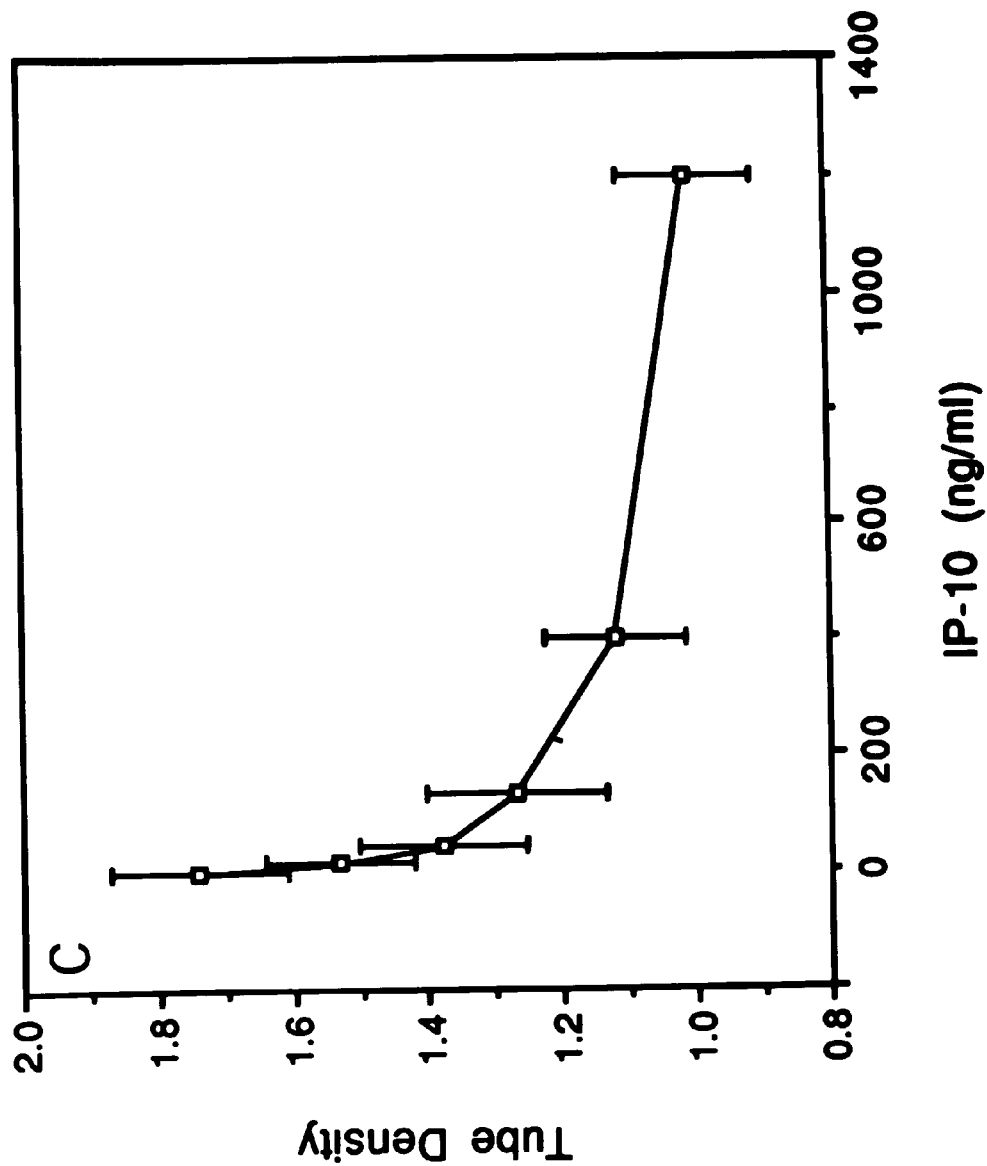

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 29 AMINO ACIDS
      (B) TYPE: AMINO ACIDS
      (D) TOPOLOGY: LINEAR (ii) MOLECULE TYPE: PEPTIDE (xi) SEQUENCE DESCRIPTION: SEQ ID NO:1:

```
Gly Glu Lys Arg Cys Leu Asn Pro Glu Ser Lys Ala
 1               5                  10

Ile Asn Lys Leu Leu Lys Ala Val Ser Lys Glu Met
            15                  20

Ser Lys Arg Ser Pro
25
```

(2) INFORMATION FOR SEQ ID NO:2:

(i) SEQUENCE CHARACTERISTICS:
      (A) LENGTH: 30 AMINO ACIDS
      (B) TYPE: AMINO ACID
      (D) TOPOLOGY: LINEAR (ii) MOLECULE TYPE: PEPTIDE (xi) SEQUENCE DESCRIPTION: SEQ ID NO:2:

```
Val Asn Pro Arg Ser Leu Glu Lys Leu Glu Ile Ile
 1               5                  10

Pro Ala Ser Gln Phe Cys Pro Arg Val Glu Ile Ile
            15                  20

Ala Thr Met Lys Lys Lys
25              30
```

(2) INFORMATION FOR SEQ ID NO:3:

(i) SEQUENCE CHARACTERISTICS:
      (A) LENGTH: 15 AMINO ACIDS
      (B) TYPE: AMINO ACID
      (D) TOPOLOGY: LINEAR (ii) MOLECULE TYPE: PEPTIDE

```
        (xi) SEQUENCE DESCRIPTION: SEQ ID NO:3:

Ser Arg Thr Val Arg Cys Thr Cys Ile Ser Ile Ser
1               5                   10

Asn Gln Pro
        15

(2) INFORMATION FOR SEQ ID NO:4:

(i) SEQUENCE CHARACTERISTICS:
            (A) LENGTH:   24 AMINO ACIDS
            (B) TYPE:  AMINO ACID
            (D) TOPOLOGY: LINEAR (ii) MOLECULE TYPE: PEPTIDE (xi) SEQUENCE DESCRIPTION: SEQ ID NO:4:

Met Asn Gln Thr Ala Ile Leu Ile Cys Cys Leu Ile
1               5                   10

Phe Leu Thr Leu Ser Gly Ile Gln Gly Val Pro Leu
            15                  20

(2) INFORMATION FOR SEQ ID NO:5:

(i) SEQUENCE CHARACTERISTICS:
            (A) LENGTH:   15 AMINO ACIDS
            (B) TYPE:  AMINO ACID
            (D) TOPOLOGY: LINEAR (ii) MOLECULE TYPE: PEPTIDE (xi) SEQUENCE DESCRIPTION: SEQ ID NO:5:

Asn Leu Leu Lys Ala Val Ser Lys Glu Met Ser Lys
1               5                   10

Arg Ser Pro
        15

(2) INFORMATION FOR SEQ ID NO:6:

(i) SEQUENCE CHARACTERISTICS:
            (A) LENGTH:   26 AMINO ACIDS
            (B) TYPE:  AMINO ACID
            (D) TOPOLOGY: LINEAR (ii) MOLECULE TYPE: PEPTIDE (xi) SEQUENCE DESCRIPTION: SEQ ID NO:6:

Pro Arg Val Glu Ile Ile Ala Thr Met Lys Lys Lys
1               5                   10

Gly Glu Lys Arg Cys Leu Asn Pro Glu Ser Lys Ala
            15                  20

Ile Lys
25

(2) INFORMATION FOR SEQ ID NO:7:

(i) SEQUENCE CHARACTERISTICS:
            (A) LENGTH:   24 AMINO ACIDS
            (B) TYPE:  AMINO ACID
            (D) TOPOLOGY: LINEAR (ii) MOLECULE TYPE: PEPTIDE (xi) SEQUENCE DESCRIPTION: SEQ ID NO:7:

Ser Ile Ser Asn Gln Pro Val Asn Pro Arg Ser Leu
1               5                   10
```

```
Glu Lys Leu Glu Ile Ile Pro Ala Ser Gln Phe Cys
        15                  20
```

(2) INFORMATION FOR SEQ ID NO:8:

(i) SEQUENCE CHARACTERISTICS:
        (A) LENGTH:  16 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:8:

```
Gly Ile Gln Gly Val Pro Leu Ser Arg Thr Val Arg
1               5                   10
Cys Thr Cys Ile
            15
```

(2) INFORMATION FOR SEQ ID NO:9:

(i) SEQUENCE CHARACTERISTICS:
        (A) LENGTH:  17 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:9:

```
Met Asn Gln Thr Ala Ile Leu Ile Cys Cys Leu Ile
1               5                   10
Phe Leu Thr Leu Ser
            15
```

(2) INFORMATION FOR SEQ ID NO:10:

(i) SEQUENCE CHARACTERISTICS:
        (A) LENGTH:  10 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:10:

```
Val Ser Lys Glu Met Ser Lys Arg Ser Pro
1               5                   10
```

(2) INFORMATION FOR SEQ ID NO:11:

(i) SEQUENCE CHARACTERISTICS:
        (A) LENGTH:  24 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:11:

```
Thr Met Lys Lys Lys Gly Glu Lys Arg Cys Leu Asn
1               5                   10
Pro Glu Ser Lys Ala Ile Lys Asn Leu Leu Lys Ala
        15                  20
```

(2) INFORMATION FOR SEQ ID NO:12:

(i) SEQUENCE CHARACTERISTICS:
        (A) LENGTH:  23 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:12:

Pro Arg Ser Leu Glu Lys Leu Glu Ile Ile Pro Ala
 1               5                  10

Ser Gln Phe Cys Pro Arg Val Glu Ile Ile Ala
        15                  20

(2) INFORMATION FOR SEQ ID NO:13:

(i) SEQUENCE CHARACTERISTICS:
        (A) LENGTH:  17 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:13:

Ser Arg Thr Val Arg Cys Thr Cys Ile Ser Ile Ser
 1               5                  10

Asn Gln Pro Val Asn
        15

(2) INFORMATION FOR SEQ ID NO:14:

(i) SEQUENCE CHARACTERISTICS:
        (A) LENGTH:  23 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:14:

Asn Pro Glu Ser Lys Ala Ile Lys Asn Leu Leu Lys
 1               5                  10

Ala Val Ser Lys Glu Met Ser Lys Arg Ser Pro
        15                  20

(2) INFORMATION FOR SEQ ID NO:15:

(i) SEQUENCE CHARACTERISTICS:
        (A) LENGTH:  20 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:15:

Phe Cys Pro Arg Val Glu Ile Ile Ala Thr Met Lys
 1               5                  10

Lys Lys Gly Glu Lys Arg Cys Leu
        15                  20

(2) INFORMATION FOR SEQ ID NO:16:

(i) SEQUENCE CHARACTERISTICS:
        (A) LENGTH:  31 AMINO ACIDS
        (B) TYPE:  AMINO ACID
        (D) TOPOLOGY:  LINEAR (ii) MOLECULE TYPE:  PEPTIDE (xi) SEQUENCE DESCRIPTION: SEQ ID NO:16:

Ser Arg Thr Val Arg Cys Thr Cys Ile Ser Ile Ser
 1               5                  10

```
Asn Gln Pro Val Asn Pro Arg Ser Leu Glu Lys Leu
            15                  20

Glu Ile Ile Pro Ala Ser Gln
25                  30
```

(2) INFORMATION FOR SEQ ID NO:17:

(i) SEQUENCE CHARACTERISTICS:
        (A) LENGTH: 21 AMINO ACIDS
        (B) TYPE: AMINO ACID
        (D) TOPOLOGY: LINEAR (ii) MOLECULE TYPE: PEPTIDE (xi) SEQUENCE DESCRIPTION: SEQ ID NO:17:

```
Thr Ala Ile Leu Ile Cys Cys Leu Ile Phe Leu Thr
1               5                   10

Leu Ser Gly Ile Gln Gly Val Pro Leu
            15                  20
```

(2) INFORMATION FOR SEQ ID NO:18:

(i) SEQUENCE CHARACTERISTICS:
        (A) LENGTH: 22 AMINO ACIDS
        (B) TYPE: AMINO ACID
        (D) TOPOLOGY: LINEAR (ii) MOLECULE TYPE: PEPTIDE (xi) SEQUENCE DESCRIPTION: SEQ ID NO:18:

```
Pro Glu Ser Lys Ala Ile Lys Asn Leu Leu Lys Ala
1               5                   10

Val Ser Lys Glu Met Ser Lys Arg Ser Pro
            15                  20
```

(2) INFORMATION FOR SEQ ID NO:19:

(i) SEQUENCE CHARACTERISTICS:
        (A) LENGTH: 17 AMINO ACIDS
        (B) TYPE: AMINO ACID
        (D) TOPOLOGY: LINEAR (ii) MOLECULE TYPE: PEPTIDE (xi) SEQUENCE DESCRIPTION: SEQ ID NO:19:

```
Val Glu Ile Ile Ala Thr Met Lys Lys Lys Gly Glu
1               5                   10

Lys Arg Cys Leu Asn
            15
```

(2) INFORMATION FOR SEQ ID NO:20:

(i) SEQUENCE CHARACTERISTICS:
        (A) LENGTH: 31 AMINO ACIDS
        (B) TYPE: AMINO ACID
        (D) TOPOLOGY: LINEAR (ii) MOLECULE TYPE: PEPTIDE (xi) SEQUENCE DESCRIPTION: SEQ ID NO:20:

```
Arg Cys Thr Cys Ile Ser Ile Ser Asn Gln Pro Val
1               5                   10

Asn Pro Arg Ser Leu Glu Lys Leu Glu Ile Ile Pro
            15                  20

Ala Ser Gln Phe Cys Pro Arg
25                  30
```

(2) INFORMATION FOR SEQ ID NO:21:

(i) SEQUENCE CHARACTERISTICS:
        (A) LENGTH: 18 AMINO ACIDS
        (B) TYPE: AMINO ACID
        (D) TOPOLOGY: LINEAR (ii) MOLECULE TYPE: PEPTIDE (xi) SEQUENCE DESCRIPTION: SEQ ID NO:21:

```
Leu Ile Phe Leu Thr Leu Ser Gly Ile Gln Gly Val
  1               5                  10

Pro Leu Ser Arg Thr Val
            15
```

INTERFERON-INDUCIBLE PROTEIN 10 IS A POTENT INHIBITOR OF ANGIOGENESIS

BACKGROUND OF THE INVENTION

Human interferon-inducible protein 10 (IP-10) is a member of the α chemokine family characterized by a CXC motif (cysteines separated by an amino acid) which include platelet factor 4 (PF-4), IL-8, human protoncogene Gro/melanocyte growth-stimulating activity, β-thromboglobulin, neutrophil-activating protein 2, and neutrophil activating protein from epithelial cells (ENA-78). IP-10 was initially described as an immediate early gene induced by IFN-γ in the histiocytic lymphoma cell line U937 (19). Activated human mononuclear cells, keratinocytes, fibroblasts, endothelial cells, and T cells also express the IP-10 gene (19). Both the human IP-10 gene and the presumed murine homologue, crg-2, code for a secreted mature protein with a predicted molecular weight of approximately 8.6 and 8.7 kD, respectively (20,21). Originally thought to be involved in inflammatory processes because of its inducibility of IFN-γ and structural similarity to PF4 and β-thromboglobulin, IP-10 appears to be multifunctional. It inhibited in vitro colony formation by human bone marrow hematopoietic cells (22) and exerted a potent antitumor effect in vivo (23). Recently, IP-10 was reported to be a chemoattractant for human monocytes and activated T lymphocytes, and to promote T cell adhesion to endothelial cells (24).

Angiogenesis, the process of generating new blood vessels leading to neovascularization, is essential during reproduction, embryonic development, tissue and organ growth, and wound healing (1). Unbalanced neovascularization is believed to contribute to the pathogenesis of certain disease states, such as arthritis, psoriasis, hemangiomas, diabetic retinopathy and retrolental fibroplasia, and to allow tumor growth and metastasis to occur (1). Tumor cells must attract new vessels to expand locally and produce metastasis (1,2).

Several compounds have been reported to inhibit endothelial cell proliferation in various experimental systems, including TGF-β (3), thrombospondin (4), IL-1 (5), γ and α IFN (6), tissue inhibitor of metalloproteinase-1 (TIMP-1) (7), platelet factor 4 (PF4) (8), protamine (9), fumagillin (10) and angiostatin (22).

Fumagillin, a product of *Aspergillus fumigatus* fresenious (10), AGM-1470, a synthetic homologue of fumagillin (10), thrombospondin (4), a matrix glycoprotein secreted by a variety of cell types, and the recently identified angiostatin, a fragment of plasminogen (25), have all been shown to potently inhibit endothelial cell proliferation in vitro and to suppress angiogenesis in vivo. IFN α and a fumagillin derivative, AGM-1470, have reached clinical testing as angiogenesis inhibitors (2). IFN-α has produced beneficial results in the treatment of certain hemangioendotheliomas (26), but the mechanisms by which it acts are poorly understood. A multistep and complex process such as angiogenesis is likely to be under multiple regulatory controls. Inhibition of angiogenesis in vivo by a drug may or may not be the result of a direct inhibition of endothelial cell growth. Curiously, TGF-β, a potent inhibitor of endothelial cell proliferation in vitro, does not inhibit, and perhaps stimulates, angiogenesis in vivo (3,15).

One of the first angiogenesis inhibitors to be identified was PF4 (8), a member of the α chemokine family. In vitro, PF4 is a potent inhibitor of growth factor dependent endothelial cell proliferation (HUVEC), albeit at high (~25 μg/ml) concentrations. PF-4 has also been shown to inhibit growth of solid tumors in vivo (U.S. Pat. Nos. 5,086,164 and 5,112,946). In contrast, another member of the α chemokine family, IL-8, was reported to stimulate umbilical vein endothelial cell proliferation in vitro and to be potently angiogenic in vivo (27,28). Thus, inhibition of angiogenesis is not a property shared among members of any of the recognized subsets of the chemokine superfamily.

Using an experimental athymic mouse model, it has been shown that regression of human Burkitt's lymphoma is induced by intratumor inoculation of Epstein-Barr virus (EBV)-immortalized human B cells (11). Extensive central necrosis associated with endothelial cell damage and intravascular thrombosis often distal to the necrotic tumor tissue is typical of regressing tumors (11). This suggested that tissue ischemia may be central to tumor regression, and raised the possibility that unbalanced angiogenesis might be responsible for regression of Burkitt's lymphoma in this system (11). Analysis of murine cytokine expression showed that IL-6, TNFα, and IP-10, but not other cytokines, are expressed at higher levels by regressing tumors compared to progressing tumors (11). However, the biological functions of IP-10 were not discerned.

The present invention demonstrates the role of IP-10 in regulation of angiogenesis in inflammation and tumor development.

SUMMARY OF THE INVENTION

The present invention is interferon-inducible protein 10 (IP-10) and fragments or analogs thereof as inhibitors of angiogenesis. Such inhibition is useful in treatment of diseases associated with increased or abnormal angiogenesis and/or endothelial cell differentiation.

The present invention also encompasses a method of inhibiting the effects of inducers of angiogenesis at a site using IP-10 alone or in combination with other therapeutic agents.

The present invention is also a method of inhibiting angiogenesis at a site of a tumor in an immunocompromised mammal by administration of an effective amount of IP-10 to inhibit angiogenesis at the tumor site in the immunocomprised mammal.

One aspect of the invention is a method of inhibiting tubular capillary structure formation using IP-10.

Another aspect of the invention is a method of inhibiting endothelial cell differentiation using IP-10.

Yet another aspect of the invention is a pharmaceutical composition comprising IP-10 alone or in combination with other therapeutic agents in a pharmaceutically acceptable carrier.

A further aspect of the invention is a method of screening for fragments and analogs of IP-10 capable of inhibiting angiogenesis or endothelial cell differentiation.

BRIEF DESCRIPTION OF DRAWINGS

These and other objects, features, and many of the attendant advantages of the invention will be better understood upon a reading of the following detailed description when considered in connection with the accompanying drawings wherein:

In FIGS. 1A, 1B and 1C the left margin coincides with the edge of the plug. Quantification of angiogenesis (FIG. 1D); results are expressed as mean matrigel surface area (x$10^3$ $\mu m^2$) occupied by cells, as determined by a semiautomated digitalized analyzer. Each dot represents the mean surface area (x$10^3$ $\mu m^2$) for each mouse and reflects 15 readings on non overlapping matrigel fields.

FIGS. 2A through 2C. Effect of IP-10 on endothelial cell differentiation. HUVEC cells (6×$10^4$) were plated on matrigel-coated 24 well plates in either complete medium alone or in complete medium supplemented with IP-10 (15 mg/ml–1200 ng/ml). After an 18 hour incubation, the cells were stained with Diff-Quick. Microscopic morphology (100× magnification) of HUVEC cultured in medium alone (FIG. 2A), and in medium supplemented with 1200 ng/ml IP-10 (FIG. 2B). Measurement of the area occupied by tube-like structure using a semi-automated digitalized analyzer (FIG. 2C); the results reflect the mean (+/−SD) of 10 separate experiments.

FIG. 5A shows characteristic features of the macrophage-rich interface separating live from dead tumor tissue and the extensive vascular damage characterized by thickening of the endothelial capillary wall and by intravascular thrombosis. FIG. 5B depicts a high power magnification of the interface separating live from dead tumor tissue. The extensive vascular pathology tissue includes complete capillary vessel obliteration with organized thrombi within live tumor tissue.

DETAILED DESCRIPTION OF THE INVENTION

Figure 1A:
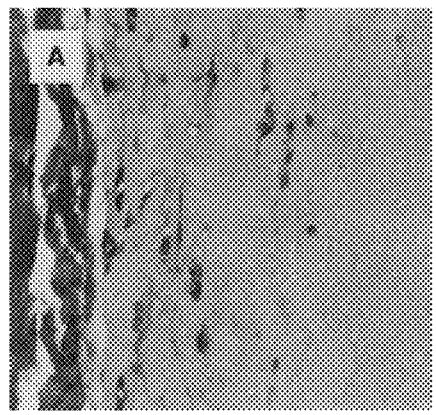
FIGS. 1A through 1D. Effect of IP-10 on neovascularization in vivo. Groups of 5 female BALB/c nu/nu mice were injected subcutaneously with matrigel alone, matrigel plus bFGF, or matrigel plus bFGF and IP-10. Plugs were removed 7 days after injection, and histologic sections were stained with Masson's trichrome. Histology (400× magnification) of a representative matrigel alone plug (FIG. 1A), matrigel plus bFGF plug (FIG. 1B), and matrigel plus bFGF and IP-10 plug (FIG. 1C).

Angiogenesis is the formation of new blood vessels. Angiogenesis occurs in a variety of physiologic and pathological processes such as embryonic growth, ovulation, cyclical development of the uterine endometrium, wound healing, inflammation, diabetic retinopathy and tumor growth.

The present invention relates to inhibition of angiogenesis by interferon-inducible protein 10 and by analogs, derivatives and fragments of IP-10 or mixtures thereof. IP-10, analogs, derivatives and fragments thereof are useful in treating angiogenic diseases in mammals so afflicted by such a disease.

Angiogenic diseases amenable to treatment using IP-10 and analogs, derivatives and fragments thereof include but are not limited to diabetic retinopathy, retrolental fibroplasia, trachoma, neovascular glaucoma, psoriases, angio-fibromas, immune and non-immune inflammation, capillary formation within atherosclerotic plaques, hemangiomas, excessive wound repair, solid tumors, Kaposi's sarcoma and the like.

IP-10 and analogs, derivatives and fragments thereof inhibit neovascularization at a site. IP-10, analogs, derivatives and fragments thereof, are effective directly or indirectly in inhibiting the function of inducers of angiogenesis. Such inducers of angiogenesis amenable to regulation by IP-10 include but are not limited to basic fibroblast growth factor (aFGF), vascular endothelial growth factor (VEGF), hepatocyte growth factor (i.e. scatter factor), IL-8 and the like. In one embodiment of the present invention, IP-10 inhibits bFGF-induced neovascularization at a site.

The present invention demonstrates that IP-10 inhibits angiogenesis at a site of tumor growth in immunocompromised or immunodeficient mammals as demonstrated in nu/nu mice. Nu/nu mice lack a thymus. Therefore, the inhibitory effect of IP-10 on tumor growth in the immunocompromise mammal is not dependent on the thymus or on T-lymphocytes. These findings are in sharp contrast to those in Luster and Leder (23) and Leder et al, Int. Pub. No. WO94/0467 (Mar. 3, 1994) who failed to demonstrate an inhibitory effect by IP-10 on tumor growth in immunodeficient mice and who teach that the IP-10 antitumor response is T-lymphocyte dependent.

IP-10 and analogs, derivatives and fragments thereof are useful therapeutics for inhibiting angiogenesis at a site of tumorigenesis or tumor growth in an immunocompromised mammal, preferably a T-lymphocyte deficient or T-lymphocyte depleted mammal. Immunocompromised mammals amenable to treatment with IP-10 include but are not limited to mammals including humans with genetic or acquired-immunodeficiency syndromes, mammals on immunosuppressive agents such as mammals pre- and post-transplantation, mammals with autoimmune diseases, mammals with viral infections and the like who are T-lymphocyte deficient or T-lymphocyte depleted. Treatment of mammals with immunosuppressive agents such as cyclosporin, anti-T cell antibodies, prednisone, irradiation, and the like for prolonged periods of time place the mammal at risk of development of tumors. IP-10 of the present invention is useful in inhibiting the angiogenesis at the site of tumorigenesis or tumor growth in these immunosuppressed mammals and in turn preventing or inhibiting tumor growth.

Patients with congenital immunodeficiency syndromes who may benefit from treatment with IP-10 include those affected by Severe Combined Immunodeficiency, Adenosine Deaminase Deficiency, DiGeorge Syndrome, Immunodeficiency with Thymoma, Immunodeficiency following hereditary defective response to Epstein-Barr virus (Purtilo Syndrome), Ataxia-telangiectasia, Wiscott-Aldrich Syndrome, or Intestinal Lymphangiectasia.

Patients with acquired immunodeficiency syndromes who may benefit from treatment with IP-10 can be distinguished in groups depending on the cause of the immunosuppression.

A. The immunosuppression may be the result of treatment with various classes of agents, including, but not limited to, a) corticosteroids; b) cytotoxic drugs, a family of drugs that includes alkylating agents (for example cyclophosphamide, chlorambucil and nitrogen mustard), purine analogs (for example azathioprine, mercaptopurine, and thioguanine) and folic acid antagonists (for instance methotrexate, and other drugs such as 5-fluorouracil, vinca alkaloid, hydroxyurea, and antibiotic immunosuppressants; c) ionizing irradiation; d) antibody therapy with anti-lymphocyte serum or monoclonal antibodies; immunosuppressive agents such as cyclosporin A; and immunosuppressive cytokines, including interferon alpha, TGF-beta, and Interleukin 10.

B. The immunosuppression may be the consequence of an acquired disease/syndrome. This includes, but is not limited to AIDS, Kaposi sarcoma, lymphomas and other malignancies in immunopriviledged sites such as the central nervous syndrome, recipients of bone marrow, stem cells, or solid organ transplants, Hodgkin's lymphoma, HTLV-1 associated T cell leukemias/lymphomas, Lupus Erythematosus, Rheumatoid arthritis, systemic vasculitis, erythema nodosum, scleroderma, Sjogren's syndrome, sarcoidosis, and primary biliary cirrhosis.

The presence of T cell immunodeficiency represents no contraindication for use of IP-10 because IP-10 was shown not to require T cells or their products to inhibit angiogenesis. Indeed the antiangiogenic effect of IP-10 was reproducibly demonstrated in athymic mice where no significant numbers of T cells and T cell functions were present. Furthermore, in vitro studies performed with primary cultures of endothelial cells alone (no other cells added), demonstrated that IP-10 disrupts the ability of endothelial cells to differentiate into tubular structures, i.e., the precursors to a mature capillary. These findings demonstrate that the antiangiogenic property of IP-10 does not require participation of T cells.

Thus, in contrast to Luster's observations, the present invention encompasses all patients who might benefit from treatment with IP-10 and exhibit various levels of congenital or acquired T cell immunodeficiency.

IP-10 inhibits endothelial cell differentiation into branching networks of tubular structures in a dose dependent fashion. IP-10 does not inhibit endothelial cell proliferation occurring either spontaneously or after induction by bFGF or ECGS (Endothelial Cell Growth Supplement), nor does it inhibit endothelial cell attachment and migration.

The present invention encompasses combination therapy in which IP-10 is administered in conjunction with another anti-angiogenic agent for inhibiting angiogenesis. Other anti-angiogenic agents that may be administered in conjunction with IP-10 include but are not limited to angiostatin, PF4, IFN-α, fumagillin, AGM-1470, thrombospondin and the like.

In one embodiment, IP-10 or analogs, derivatives and fragments thereof are administered in combination with platelet factor 4 (PF4) for inhibition of angiogenesis. In such a combination therapy, IP-10 inhibits endothelial cell differentiation and PF4 inhibits endothelial cell proliferation for an enhanced anti-angiogenic effect.

In another embodiment, IP-10 or analogs, derivatives and fragments thereof are administered in combination with angiostatin for a synergistic or additive anti-angiogenic effect. Combination therapy with an antiangiogenic factor that inhibits endothelial cell proliferation and IP-10 that inhibits endothelial cell differentiation into vessels is particularly beneficial.

Combination therapy is not limited to the use of IP-10 in conjunction with another anti-angiogenic agent but encompasses therapy using IP-10 in combination with an anti-inflammatory agent such as ibuprofen, aspirin, prednisone, and the like.

Combination therapy also encompasses the use of IP-10 in combination with a chemotherapeutic agent such as Taxol, cyclophosphamide, cisplatin, gancyclovir and the like. Such a therapy is particularly useful in situations in which the mammal to be treated has a large preexisting tumor mass which is well vascularized. The chemotherapeutic agent serves to reduce the tumor mass and the IP-10 prevents or inhibits neovascularization within or surrounding the tumor mass.

IP-10 for use in the present invention may be obtained from natural, recombinant or synthetic sources. In the case of natural sources, IP-10 may be purified and isolated from any mammalian species, preferably from human sources. Analogs according to the invention may include peptides with conservative amino acid substitutions or non-conservative amino acid substitutions, deletions or insertions which do not lessen the anti-angiogenic activity of the IP-10. The invention also includes IP-10 coupled to carbohydrates such as PEG or protein carriers as long as the analog retains its anti-angiogenic function. Sarris et al. disclose production of human recombinant IP-10 (22). Synthetic fragments of IP-10 may be made by standard methods of peptide synthesis as are known in the art.

Peptides of IP-10 having less than 35 amino acids, preferably less than 25 amino acids, more preferably in a range of 10–15 amino acids may retain the antiangiogenic activity of the intact IP-10 molecule. Peptides of IP-10 encompassed by the present invention include but are not limited to one or more of the following peptides:

GEKRCLNPESKAIKNLLKAVSKEMSKRSP (SEQ ID NO.: 1);
VNPRSLEKLEIIPASQFCPRVEIIATMKKK (SEQ ID NO.: 2)
SRTVRCTCISISNQP (SEQ ID NO.: 3);
MNQTAILICCLIFLTLSGIQGVPL (SEQ ID NO.: 4);
NLLKAVSKEMSKRSP (SEQ ID NO.: 5);
PRVEIIATMKKKGEKRCLNPESKAIK (SEQ ID NO.: 6);
SISNQVNPRSLEKLEIIPASFC (SEQ ID NO.: 7);
GIQGVPLSRTVRCTCI (SEQ ID NO.: 8);
MNQTAILICCLIFLTLS (SEQ ID NO.: 9);
VSKEMSKRSP (SEQ ID NO.: 10);
TMKKKGEKRCLNPESKAIKNLLKA (SEQ ID NO.: 11);
PRSLEKLEIIPASQFCPRVEIIA (SEQ ID NO.: 12);
SRTVRCTCISISNQPVN (SEQ ID NO.: 13);
NPESKAIKNLLKAVSKEMSKRSP (SEQ ID NO.: 14);
FCPRVEIIATMKKKGEKRCL (SEQ ID NO.: 15);
SRTVRCTCISISNQPVNPRSLEKLEIIPASQ (SEQ ID NO.: 16);
TAILICCLIFLTLSGIQGVPL (SEQ ID NO.: 17);
PESKAIKNLLKAVSKEMSKRSP (SEQ ID NO.: 18);
VEIIATMKKKGEKRCLN (SEQ ID NO.: 19);
RCTCISISNQPVNPRSLEKLEIIPASQFCPR (SEQ ID NO.: 20);
LIFLTLSGIQGVPLSRTV (SEQ ID NO.: 21) and combinations and mixtures thereof. Also emcompassed in the present invention are peptides comprised of one or more of the above sequences repeated at least twice in the peptides. Further emcompassed in the invention are one or more of the peptides of IP-10 attached to a carrier or ligand. In addition, modifications within these minimal peptides of IP-10 may also retain the antiangiogenic activity or may even show increased activity (if any inhibitory portions of the molecule are eliminated).

Recombinant PF4 (rPF4), synthetic peptides and modified peptides of PF4 may be prepared as disclosed in U.S. Pat. No. 5,086,164 and U.S. Pat. No. 5,112,946.

Angiostatin may be prepared from natural sources as described (25) or may be produced through recombinant technologies.

IP-10 of the present invention is useful in inhibiting the angiogenic function of target cells both in vitro and in vivo. IP-10 of the present invention is particularly useful in inhibiting the angiogenic function of endothelial cells both in vitro and in vivo. Of particular interest is the prevention or inhibition of endothelial cell differentiation into capillary structures. The endothelial cells amenable to inhibition by IP-10 are present at several sites in a mammal and include but are not limited to dermis, epidermis, endometrium, retina, surgical sites, gastrointestinal tract, liver, kidney, reproductive system, skin, bone, muscle, endocrine system, brain, lymphoid system, central nervous system, respiratory system, umbilical cord, breast tissue, urinary tract and the like. The method of treatment of the present invention using IP-10 is particularly useful in preventing or inhibiting angiogenesis by endothelial cells at sites of inflammation and tumorigenesis.

Angiogenesis associated with autoimmune diseases may be treated using IP-10. The autoimmune diseases include but are not limited to rheumatoid arthritis, systemic lupus erythematosus, thyroiditis, Goodpasture's syndrome, systemic vasculitis, scleroderma, Sjogren's syndrome, sarcoidosis, primary biliary cirrhosis and the like.

Angiogenesis associated with wound repair may also be treated using IP-10. Excessive scarring resulting from excess angiogenesis often occurs at sites of skin trauma or surgical sites. Administration of IP-10 at the site is useful in preventing or inhibiting angiogenesis at the site to eliminate or lessen the scarring.

IP-10 is also useful in methods of inhibiting angiogenesis at a site of tumorigenesis in an immunocompromised mammal. IP-10 administered at such sites prevents or inhibits blood vessel formation at the site thereby inhibiting the development and growth of the tumor. Tumors which may be prevented or inhibited by preventing or inhibiting angiogenesis with IP-10 include but are not limited to melanoma, metastases, adenocarcinoma, sarcomas, thymoma, lymphoma, lung tumors, liver tumors, colon tumors, kidney tumors, non-Hodgkins lymphoma, Hodgkins lymphoma, leukemias, uterine tumors, breast tumors, prostate tumors, renal tumors, ovarian tumors, pancreatic tumors, brain tumors, testicular tumors, bone tumors, muscle tumors, tumors of the placenta, gastric tumors and the like.

In the method of treatment, the administration of IP-10, analogs, derivatives or fragments thereof may be for either "prophylactic" or "therapeutic" purpose. When provided prophylactically, the IP-10 is provided in advance of any symptom. The prophylactic administration of the IP-10 serves to prevent or inhibit any angiogenesis at a site. When provided therapeutically, the IP-10 is provided at (or after) the onset of a symptom or indication of angiogenesis. Thus, IP-10 may be provided either prior to the anticipated angiogenesis at a site or after the angiogenesis has begun at a site.

The term "unit dose" as it pertains to an inoculum refers to physically discrete units suitable as unitary dosages for mammals, each unit containing a predetermined quantity of IP-10, analogs, derivatives or fragments thereof calculated to produce the desired inhibitory effect in association with a diluent. The specifications for the novel unit dose of an inoculum of this invention are dictated by and are dependent upon the unique characteristics of the IP-10 and the particular effect to be achieved.

The inoculum is typically prepared as a solution in tolerable (acceptable) diluent such as saline, phosphate-buffered saline or other physiologically tolerable diluent and the like to form an aqueous pharmaceutical composition. In addition, the IP-10, analogs, derivatives or fragments thereof may be formulated in solid form and lyophilized form and redissolved or suspended prior to use.

The route of administration may be intravenous (I.V.), intramuscular (I.M.), subcutaneous (S.C.), intradermal (I.D.), intraperitoneal (I.P.), intrathecal (I.T.), intrapleural, intrauterine, rectal, vaginal, topical, intratumor and the like.

Administration may be by transmucosal or transdermal means. For transmucosal or transdermal administration, penetrants appropriate to the barrier to be permeated are used in the formulation. Such penetrants are generally known in the art, and include, for example, for transmucosal administration bite salts and fusidic acid derivatives. In addition, detergents may be used to facilitate permeation. Transmucosal administration may by through nasal sprays, for example, or using suppositories. For oral administration, IP-10 is formulated into conventional oral administration forms such as capsules, tablets and tonics.

For topical administration, IP-10 is formulated into ointments, salves, gels, or creams, as is generally known in the art.

In providing a mammal with the IP-10, preferably a human, the dosage of administered IP-10 will vary depending upon such factors as the mammal's age, weight, height, sex, general medical condition, previous medical history, disease progression, tumor burden, route of administration, formulation and the like.

In general, it is desirable to provide the recipient with a dosage of IP-10 of at least about 0.1 mg/kg, preferably at least about 25 mg/kg, more preferably at least about 50 mg/kg or higher. A range of from about 1 mg/kg to about 100 mg/kg is preferred although a lower or higher dose may be administered. The dose provides an effective antiangiogenic serum or tissue level of IP-10. The dose is administered at least once and may be provided as a bolus or a continuous administration. Multiple administration over a period of weeks may be preferable. It may also be preferable to administer IP-10 at least once/week and even more frequent administrations (eg. daily) may yield yet more preferable results. Subsequent doses may be administered as indicated.

The studies in nude mice indicate that IP-10 is well tolerated when injected intratumor daily for 5 days/week at a doses ranging from about 200 and about 800 nanograms/animal over a period of 5 to 7 weeks. IP-10 was also well tolerated when injected in nude mice intraperitoneally daily for about 10 to about 15 days at a dose of 1 microgram/animal, for a total cumulative dose of 10 to 15 micrograms.

These doses of IP-10 used safely in mice translate to a total cumulative dose in humans of about 1.0 to about 1.5 mg/kg, or approximately 3.9 mg/m$^2$. Thus, doses of IP-10 for intratumor injection in humans are at least about 0.1 mg/kg, preferably at least about 25 mg/kg more preferably at least about 50 mg/kg or higher. A dose in the range of about 1 mg/kg to about 100 mg/kg is preferred although higher and lower doses may be used. The duration of treatment may be from days to weeks depending on the dose and size of the tumor.

Intratumor administration of IP-10 was effective in reducing tumor size when given to nude mice at doses ranging between about 100 and 800 nanograms/animal daily for five days/week for 5 to 7 weeks. However, 1 microgram/mouse of IP-10 given intraperitoneally daily for up to 15–20 days was ineffective in reducing tumor size in the same nude mouse model. Thus, effective therapy with IP-10 may require different doses depending upon the routes of administration, systemic administrations requiring higher IP-10 concentrations to be effective.

It may be appropriate to modify IP-10 by attaching compounds, such as but not limited to PEG, to prolong its half-life without diminishing its anti-angiogenic property.

In addition to targeting IP-10 to the sites where it is most needed by injection or topical application, chimeric proteins composed of IP-10 plus a ligand to appropriate surface determinants may be used to target IP-10 to a specific site or a specific cell type. In one embodiment, a chimeric protein is composed of the IP-10 biologically active component and a ligand for endothelial cells, such as the combining site of an antibody to the endothelial cell surface component CD31 or ligands for the FGF receptors.

In another approach to specific IP-10 targeting and sustained dosing, constructs of the IP-10 gene in appropriate vectors are used for gene expression of IP-10 in selected tissues, including endothelial cells. For example, one construct in which replication deficient adenovirus vectors encoding a recombinant secreted IP-10 protein are prepared. These IP-10 expressing adenovirus vectors are injected at the desired site, or in proximity of the desired site to cause endothelial cell infection with adenovirus and local secretion of the therapeutic IP-10 protein expressed in the infected endothelial cells.

For combination therapy, the dose of IP-10 may be administered prior to, concurrently, or after administration of a second anti-angiogenic agent, anti-inflammatory agent or chemotherapeutic agent.

The dose of a second anti-angiogenic agent for administration in combination with IP-10 is at least about 0.1 mg/kg, preferably at least about 25 mg/kg, more preferably at least about 50 mg/kg or higher.

The dose of an anti-inflammatory agent or chemotherapeutic agent for administration in combination with IP-10 are doses routinely used in the art.

The present invention also encompasses a pharmaceutical composition capable of inhibiting angiogenesis which comprises IP-10, analogs, derivatives or fragments thereof in a pharmaceutically acceptable carrier. The pharmaceutical composition may additionally comprise a second anti-angiogenic agent including but not limited to angiostatin, PF4, IFN-a, fumagillin, AGM-1470, thrombospondin, and the like or mixtures thereof. Moreover, the pharmaceutical composition, in addition to IP-10, may also include an anti-inflammatory agent such as ibuprofen, aspirin, prednisone, and the like or mixtures thereof.

In another embodiment, the pharmaceutical composition also includes a chemotherapeutic agent such as taxol, cyclophosphamide, cisplatin, gancyclovir, and the like or mixtures thereof.

IP-10 may be administered in the form of a chimeric protein comprising the biologically active portion of IP-10 and a ligand. The ligand may be a growth factor, chemokine, growth factor receptor, antibody and the like that targets IP-10 to a specific site, protein or cell type. Administration of the IP-10 chimeric protein allows for efficient targeting of IP-10 to a site. For example, the ligand comprising the chimeric protein may be a modified bFGF protein that binds to the FGF receptor but does not cause angiogenesis. In another example, the chimeric protein may include a ligand for the endothelial cell surface molecule CD31 or other endothelial cell ligands.

The efficacy of treatment may be assessed by various parameters including 1) tumor size reduction, as determined by measurement of cutaneous masses (such as melanoma, Kaposi sarcoma, etc.), X-rays, scans and other means of tumor size evaluation; 2) lack of tumor progression, as evaluated by the methods listed above; 3) reduced keloid formation, as determined by measurement and evaluation of superficial lesions; 4) improvement of retinal lesions associated with diabetic retinopathy, as determined by comparative analysis of photographs of the retinal fundus and other appropriate methods of evaluation; 5) lack of progression of diabetic retinopathy as determined by the method listed above. Blood pharmacological levels of IP-10 may be determined by ELISA, capture assays, radioimmunoassays and receptor binding assays and the like.

The methods described herein are useful in screening analogs, derivatives, fragments and chimeric protein of IP-10 for anti-angiogenic activity.

It is understood that the examples and embodiments described herein are for illustrative purposes only and that various modifications or changes in light thereof will be suggested to persons skilled in the art and are to be included within the spirit and purview of this application and scope of the appended claims.

The references and patents referred to are incorporated herein by reference.

EXAMPLE 1

Material and Methods

Mice, Cells, Reagents, and Cytokines

Four- to six-week-old female BALB/c nu/nu mice (Charles River Laboratories, Wilmington, Mass. or National Cancer Institute, Frederick, Md.) maintained in pathogen-limited conditions were used throughout. Matrigel was extracted from the Englebreth-Holm-Swarm (EHS) tumor as previously described (12). Matrigel may also be purchased from commercial sources such as Collaborative Research, Bedford, Mass. Recombinant human IP-10 (0.06 Endotoxin Units/μg, Pepro Tech Inc., Rocky Hill, N.J.) was either purchased or provided by the National Cancer Institute, Frederick, MD. TGF-β was obtained from R&D Systems (Minneapolis, Minn.). The human Mig (monokine induced by INF-γ) protein was the mature, 103 amino acid recombinant protein (U.S. Pat. No. 5,236,829) purified from an overexpressing chinese hamster ovary cell line as described by Liao, F., R. Rabin, L. Koniaris, P. Vanguri, J. Yannelli, and J. Farber (manuscript submitted). Mig concentration was determined using the Bradford assay (Bio-Rad Laboratories, Hercules, Calif.) standardized with BSA. Recombinant human IL-8 was obtained from Biosource International (Camarillo, Calif.). Recombinant human MCAF (macrophage chemotactic and activating factor) and recombinant human RANTES (Regulated on Activation, Normal T-cell Expressed, and Secreted) were obtained from Pepro Tech Inc.; recombinant human PF4 (Platelet Factor-4) was obtained from Repligen Co. (Cambridge, Mass.). Fetal bovine heart endothelial cells (FBHE) (ATCC CRL 1395) [American Type Culture Collection (ATCC), Rockville, Md.] were grown in DMEM (Biofluids Inc., Rockville, Md.) containing 10% heat inactivated fetal bovine serum (FBS) (Intergen Co., Purchase, N.Y.), 100 ng/ml bFGF (R&D Systems), and 5 μg/ml gentamicin (Sigma Chemical Co., St. Louis, Mo.). Human umbilical vein endothelial cells (HUVEC), from ATCC (ATCC CRL 1730) or provided by the National Institute of Dental Research, were maintained in RPMI 1640 Medium (Gibco, BRL, Grand Island, N.Y.), 15% FBS, 20 U/ml porcine preservative free heparin (Squibb-Marsam Inc., Cherry Hill, N.J.), and 100 μg/ml endothelial cell growth supplement (ECGS, a crude extract of bovine neural tissue containing bFGF and aFGF, Calbiochem-Novabiochem Corp. LaJolla, Calif.). H5V, a murine heart endothelioma cell line, was a gift from Dr. A. Mantovani, Instituto di Ricerche Farmacologiche, Milan, Italy (13). Similar cell lines may be prepared as described by Garlanda et al (13). CD3-21, a murine pulmonary microvascular endothelial cell line was kindly provided by Dr. C. Diglio, Wayne State University, Detroit, Mich. (14). Similar cell lines may be prepared as described by Chopra et al (14). Both H5V and CD3-21 cells were grown in DMEM, 10% FBS, and 5 μg/ml gentamicin.

In Vivo Matrigel Assay

This assay was performed as described (15). Briefly, matrigel (liquid at 4° C.) was mixed with 150 ng/ml bFGF alone or in combination with IP-10, TGF-β, IL-8, Mig, RANTES or MCAF each at a final concentration of 400 ng/ml. Matrigel alone or with bFGF or with bFGF plus the test cytokine (total volume 0.5 ml) was injected subcutaneously into the midabdominal region of the BALB/c nude mouse. After injection, the matrigel polymerizes to form a plug. After 7 days, the animals were sacrificed, the matrigel plugs removed together with the abstract epidermis and dermis, fixed in 10% neutral buffered formalin solution (Sigma Chemical Co.), and embedded in paraffin. Histological sections were stained with Masson's trichrome. The vessel area in the histological sections were measured using an Optomax Computerized digital analyzer (Optomax Inc., Hollis, N.H.) as described (15). The mean area per field ($X10^3$ $\mu m^2$) from 15 fields (20x) was calculated.

Cell Proliferation

FBHE, HUVEC, H5V and CD3-21 cells were used routinely before the 15th passage. After trypsinization, the cells were plated in triplicate cultures of $1 \times 10^3$ or $8 \times 10^3$ cells in 0.2 ml complete medium with or without additives in a 96-well flat-bottom plate. The plates were incubated for 1–7 days. DNA synthesis was determined by [$^3$H]-thymidine deoxyribose uptake (0.5 uCi/well, 6.7 Ci/mmol; New England Nuclear, Boston, Mass.) during the last 6 or 18 hours of culture. Cells were detached by freezing/thawing.

Cell Attachment Assay

This assay was performed as described (16). HUVEC cells were plated (in 4 replicates, $4 \times 10^4$ cells/well in complete medium) on BSA-precoated 48-well plates and IP-10 added at final concentrations of 0, 15, 45, 135, 400 or 1200 ng/ml. After incubation for 1 h, the supernatant was aspirated, and the cells were fixed and stained using Diff-Quick (Baxter Scientific Products, McGraw Park, Ill.).

Cell Migration Assay

Cell migration was measured as described (17). Two 2 mm scratches were made in each well of a 6 well plate containing confluent HUVEC using a modified rubber cell scrapper. The wells were rinsed, and 1.5 ml complete medium containing 0, 15, 45, 135, 400 or 1200 ng/ml IP-10 was added. After 24 h incubation, 2 additional scratches per well were made as referenced marks, the medium was aspirated, and the cells were fixed and stained using Diff-Quick. Cell migration into the scratched area was evaluated under an inverted phase microscope.

Endothelial Tube Formation on Matrigel

Tube formation was evaluated as described (18). Matrigel (320 $\mu$l/well), used at 4° C. to coat a 24-well plate, was allowed to polymerize at 37° C. for 2 hours. HUVEC, $4$–$6 \times 10^4$ cells/well, in a final volume of 1 ml HUVEC complete medium containing 0, 15, 45, 135, 400 or 1200 ng/ml IP-10 were plated on the matrigel substratum. After an 18 h incubation, the medium was aspirated, and the adherent cells were fixed and stained using Diff-Quick. Tube formation was examined visually and total tube area per well was quantitated by the Optomax digital analyzer. The assay was performed in duplicate.

Statistical Analysis

Arithmetic means, standard deviations, and Student's t tests were calculated by conventional formulas using Systat for the Macintosh (Systat Inc., Evanston, Ill.).

EXAMPLE 2

IP-10 Inhibits Neovascularization In Vivo

Figure 1B:
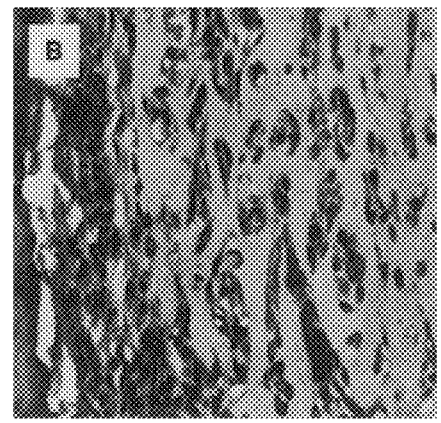
Figure 1C:
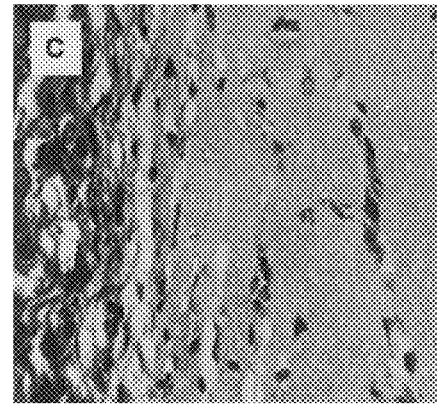
Figure 1D:
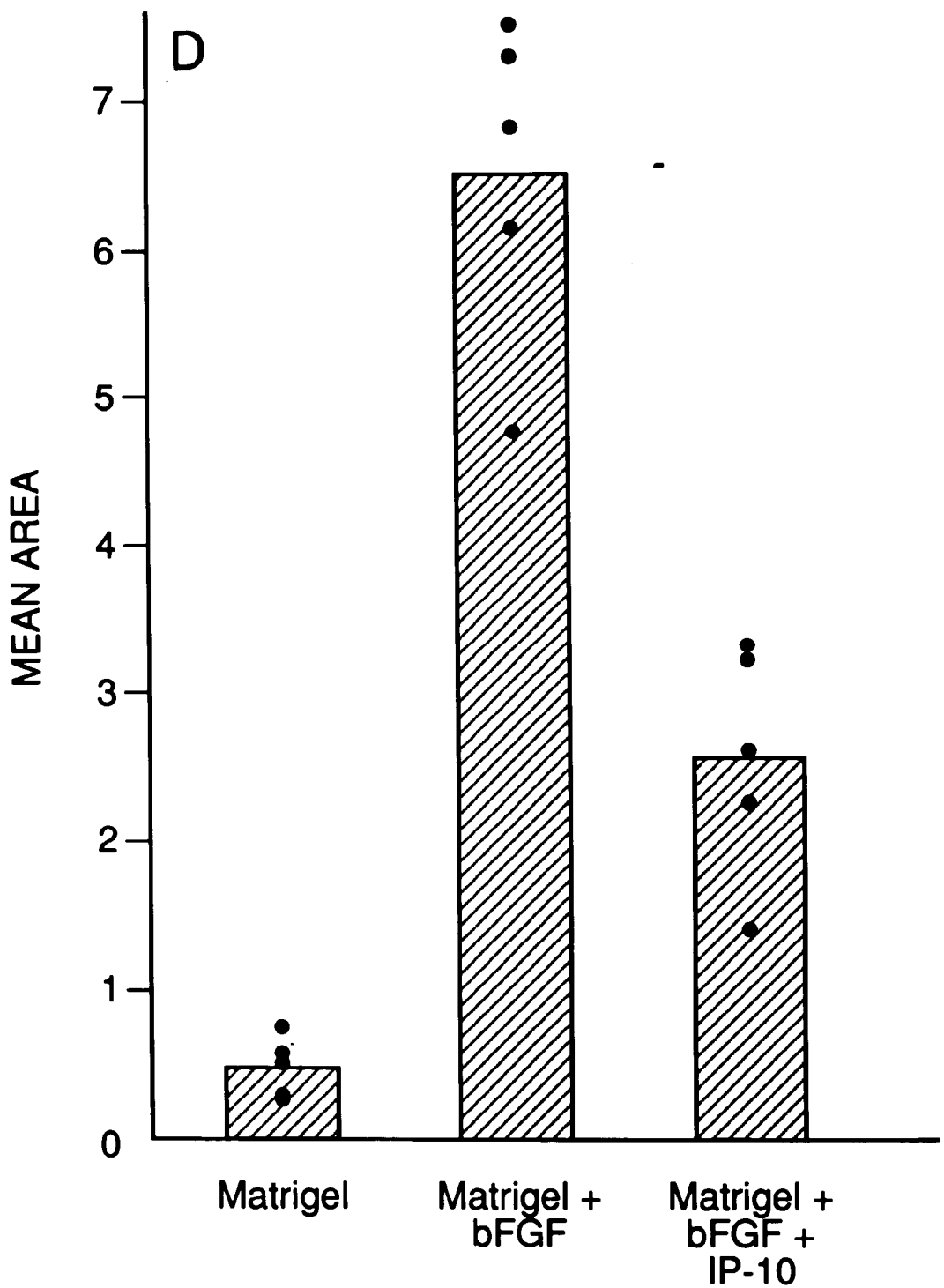

To assess the effects of IP-10 on neovascularization in vivo, a mouse model was used in which subcutaneous injection of matrigel impregnated with bFGF rapidly induces new vessel formation (15). The results of a representative experiment in which groups of athymic mice were injected either with A) matrigel alone (0.5 ml), B) matrigel (0.5 ml) plus bFGF (150 ng/ml), or C) matrigel (0.5 ml) plus bFGF (150 ng/ml) plus IP-10 (400 ng/ml) are depicted in FIGS. 1A through 1C. Microscopic examination of the matrigel plugs removed from the mice 7 days after injection revealed the presence of only few endothelial cells invading the matrigel alone plug (FIG. 1A). In contrast, abundant endothelial cells, often organized to form blood vessels containing red blood cells, were present in the matrigel plus bFGF plug (FIG. 1B). Addition of IP-10 to matrigel plus bFGF resulted in marked reduction in the number of endothelial cells invading the plug and the absence of blood vessels (FIG. 1C). Quantitative analysis of this experiment, which included 5 nude mice per treatment group, is shown in FIG. 1D. Plugs of matrigel alone contained very few endothelial cells (mean surface area $483.8 \times 10^3$ $\mu M^2$). Matrigel plugs impregnated with bFGF contained approximately 13-fold more cells compared to plugs of matrigel alone (mean surface area $6511.2 \times 10^3$ $\mu m^2$). Matrigel plugs with IP-10 added together with bFGF contained significantly fewer cells compared to matrigel plus bFGF plugs (mean surface area $2568.0 \times 10^3$ $\mu m^2$, p=0.0002). These experiments demonstrated that IP-10 acts as a potent inhibitor of bFGF-induced neovascularization in vivo.

Tests were conducted to determine whether other cytokines/chemokines might also act as inhibitors of neovascularization measured by this in vivo assay system. As shown in Table 1, IP-10 consistently inhibited neovascularization of matrigel plugs containing bFGF. When added to matrigel alone, without bFGF, IP-10 had at most a slight inhibitory effect. Mig and IL-8, two additional members of the α chemokine family, had little or no inhibitory effect on angiogenesis induced by bFGF and matrigel. RANTES and MCAF, members of the β chemokine family, had no inhibitory effect on neovascularization induced by bFGF and matrigel. As reported (15), TGF-β had little or no effect on neovascularization in this assay system. These experiments demonstrated that IP-10 is a potent inhibitor of neovascularization induced by bFGF in vivo. The data also shows that inhibition of angiogenesis is not common to all chemokines.

TABLE 1

Effects of Cytokines/Chemokines on Angiogenesis in Vivo

| Additions to Matrigel | Mean Surface Area (x $10^3$ $\mu m^2$) | (± SD) |
|---|---|---|
| None | 554 | 196 |
| bFGF | 5,511 | 1,404 |
| bFGF + IP-10 | 1,317 | 389 |
| IP-10 | 355 | 128 |
| None | 484 | 209 |
| bFGF | 6,511 | 1,097 |
| bFGF + IP-10 | 2,568 | 769 |
| bFGF + TGF-β | 9,131 | 2,113 |
| None | 997 | 34 |
| bFGF | 7,060 | 820 |
| bFGF + IP-10 | 2,118 | 447 |
| bFGF + IL-8 | 5,662 | 867 |
| bFGF + Mig | 6,303 | 824 |
| None | 665 | 152 |
| bFGF | 6,140 | 854 |
| bFGF + IP-10 | 1,826 | 858 |
| bFGF + RANTES | 5,856 | 657 |
| bFGF + MCAF | 6,196 | 820 |

BALB/c nu/nu female mice (5 mice per condition in each experiment) were injected subcutaneously with either matrigel alone (0.5 ml), matrigel plus bFGF (150 ng/ml), matrigel plus IP-10 (400 ng/ml), or matrigel plus bFGF (150 ng/ml) plus one of the indicated cytokine/chemokines (all at 400 ng/ml). The matrigel plugs were removed after 7 days and processed for histology. The results reflect the mean matrigel surface area occupied by cells (+/− SD) for each group of mice.

EXAMPLE 3

Effects of IP-10 on Endothelial Cell Proliferation, Cell Attachment, Migration and Differentiation Angiogenesis is known to be a complex process that requires endothelial cell proliferation, migration and differentiation into tube-like structures (1). Since IP-10 inhibited angiogenesis in vivo, tests were conducted to dissect its mode of action. First, it was determined whether IP-10 inhibits endothelial cell proliferation. HUVEC and FBHE are growth factor-dependent primary endothelial cell cultures found to grow optimally in vitro with ECGS (Endothelial Cell Growth Supplement) and bFGF, respectively. The murine heart endothelioma cell line H5V and the murine pulmonary microvascular endothelial cell line CD3-21 are immortalized, growth factor-independent endothelial cell lines. IP-10 (400 ng/ml) had little or no effect on the proliferation of growth factor (bFGF or ECGS)-induced and spontaneous endothelial cell proliferation when measured after 7 days of culture (Table 2). Also, IP-10 had little or not effect on growth factor-induced HUVEC proliferation when measured after 30 hours of culture, even at 2 μg/ml and in the absence of heparin. As expected, TGF-β inhibited bFGF-induced proliferation of FBHE cells, and PF4 in the absence of heparin, inhibited the proliferation of HUVEC at 40 μg/ml but not 2 μg/ml. Time course experiments (not shown) confirmed that IP-10 failed to inhibit endothelial cell proliferation at earlier time points (1, 3, and 5 days). Dose response experiments (not shown) demonstrated that IP-10 failed to inhibit endothelial cell growth even at doses ranging between 10 ng/ml and 2 μg/ml. Thus IP-10 is not an inhibitor of endothelial cell growth in vitro, suggesting that inhibition of cell division is not the mechanism by which IP-10 inhibits angiogenesis in vivo.

TABLE 2

Effects of IP-10 on endothelial cell proliferation in vitro

| Additions to Culture | Proliferation Exp 1 | (cpm/culture)** Exp 2 |
|---|---|---|
| FBHE* | | |
| Medium | 1,094 | 1,294 |
| bFGF | 8,667 | 10,664 |
| bFGF + IP-10 (400 ng/ml) | 8,298 | 9,421 |
| bFGF + TGF-β (10 ng/ml) | 193 | 315 |
| HUVEC* | | |
| Medium | 253 | 191 |
| ECGF | 8,648 | 7,965 |
| ECGF + IP-10 (400 ng/ml) | 6,315 | 8,050 |
| ECGF + TGF-β (10 ng/ml) | 6,441 | 7,138 |
| H5V* | | |
| Medium | 71,753 | 116,102 |
| Medium + IP-10 (400 ng/ml) | 70,148 | 108,276 |
| Medium + TGF-β (10 ng/ml) | n.d. | 72,548 |
| CD3-21* | | |
| Medium | 755 | 695 |
| Medium + IP-10 (400 ng/ml) | 833 | 754 |
| Medium + TGF-β (10 ng/ml) | 724 | n.d. |
| HUVEC‡ | | |
| Medium | 254 | 395 |
| ECGF | 1,082 | 915 |
| ECGF + IP-10 (2 μg/ml) | 1,092 | 1,784 |
| ECGF + PF 4 (2 μg/ml) | 979 | 674 |
| ECGF + PF4 (40 μg/ml) | 406 | 546 |

*The endothelial cells/cell lines FBHE, HUVEC, H5V and CD3-21 (1 × 10³ cells/0.2 ml well) were cultured for 7 days with or without IP-10, or TGF-β.
‡HUVEC (8 × 10³ cells/0.2 ml well) were cultured without heparin for 30 h with or without IP-10 or PF4.
**[³H]-thymidine was added during the final 18 h of culture. The results are expressed as mean cpm of triplicate cultures (SDs within 12% of the mean). n.d. denotes not done.

To assess whether IP-10 interferes with the migration and attachment of endothelial cells, HUVEC cells were tested for their ability to attach to BSA-coated plastic wells (16) and to migrate (17), in the presence or absence of IP-10 (15–1200 ng/ml). As measured in these assays, neither endothelial cell attachment nor migration were affected by IP-10 at all tested doses (results not shown).

Figure 2A:
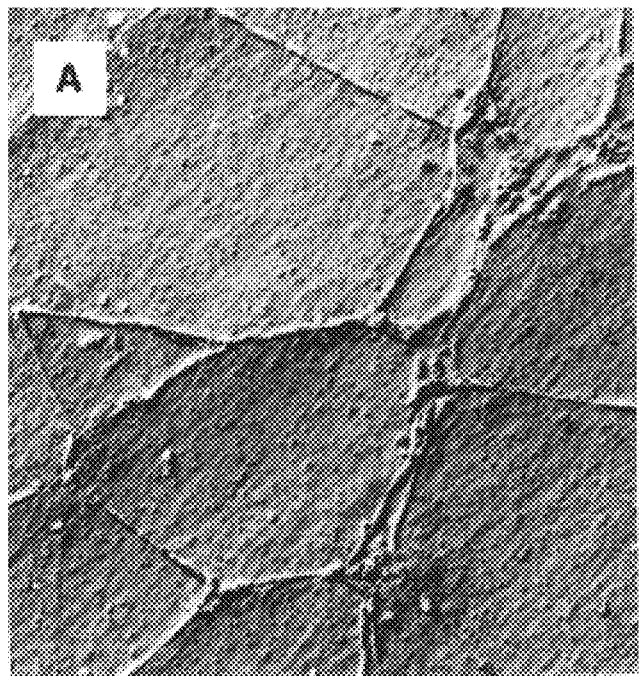
Figure 2B:
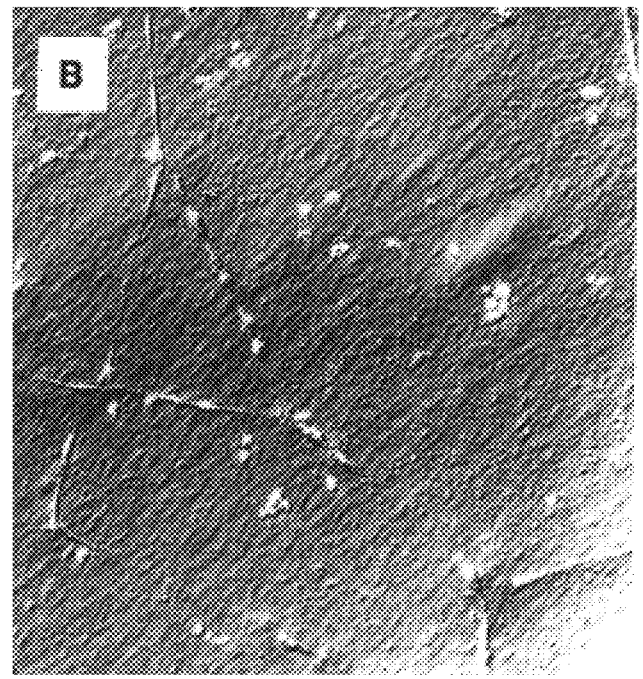

Tests were conducted to determine whether IP-10 inhibits the differentiation of endothelial cells into tube-like structures, an essential step to new blood vessel formation (16). As reported (16), when endothelial cells (HUVEC) were cultured for 12–18 hours on a matrigel substrate, they rapidly aligned with one another and formed an intricate network of tube-like structures (FIG. 2A). In the presence of IP-10, the endothelial cells formed small aggregate structures, and the network of tube-like structures was strikingly less extensive than in control cultures (FIG. 2B). This effect of IP-10 was not due to inhibition of endothelial cell attachment to the matrigel monolayer or to inhibition of cell survival/proliferation during incubation, because at the end of culture with or without IP-10 both similar numbers of nonadherent cells were recovered (approximately 10% of the initial input), and similar numbers of nuclei were counted on the matrigel monolayer. Measurement of the total tube area by a semi-automated digital analyzer confirmed the visual observation that IP-10 inhibits endothelial cell differentiation into tube-like structures (FIG. 2C). This effect was dose-dependent, and the surface area reduction was significant at all IP-10 doses tested (p≦0.0001). These experiments demonstrated that IP-10 inhibits endothelial cell differentiation into capillary-like structures in vitro, and suggested a mechanism whereby IP-10 inhibits angiogenesis in vivo.

EXAMPLE 3

Anti-Angiogenic Effect of Interferon-Inducible Protein 10 at a Site of Tumorigenesis To further assess the effects of IP-10 on neovascularization in vivo, a nude mouse model was utilized in which neovascularization is induced by subcutaneous injection of human Burkitt's lymphoma cell lines (11). When injected subcutaneously into athymic mice, human Burkitt's lymphoma cell lines generally develop into progressively growing subcutaneous tumors. Tumor progression is associated with neovascularization that provides a mechanism by which nutrients are delivered to the progressively growing tumor tissue. Insufficient neovascularization can cause tumor cells to die in situ, followed by decreased tumor growth and/or tumor regression.

In previous studies, it has been demonstrated that inoculation of human EBV-immortalized B lymphocytes into established human Burkitt's lymphomas is associated with regression of the Burkitt's tumors and cure of the nude mouse (11). Histogical examination of the regressing tumors showed massive central necrosis extending to the epidermis, surrounded by viable lymphoid cells, presumably representing residual tumor cells. Infiltration with some histiocytes was seen within and at the periphery of the tumor. But the most characteristic feature of the regressing tumors is the presence of intravascular thrombosis, thickening of the endothelium and endothelial cell damage localized both at the margin as well as within live tumor tissue (11). These histological findings suggested that vascular endothelium damage and secondary tumor tissue ischemia may be central to tumor regression in this system.

To assess the effects of IP-10 as an inhibitor of angiogenesis in vivo, recombinant human IP-10 (Pepro Tech Inc., Rocky Hill, N.J.) as inoculated into established human Burkitt's lymphoma tumors. First, groups of sublethally irradiated athymic mice were inoculated with $10^6$ human Burkitt's lymphoma cells in the subcutaneous tissues and the appearance of tumors was observed. Once the tumors reached at least 0.25 cm$^2$ in size, the mice were either observed or inoculated intratumor with IP-10 or buffer alone (0.1 ml/injection). As a control, groups of mice were simultaneously injected with Epstein-Barr virus-immortalized human B cell lines and Burkitt's lymphoma cells. The results of representative experiments are shown in Table 3. As expected, athymic mice injected subcutaneously with $10^6$ Burkitt's lymphoma cells developed progressively growing tumors without evidence of tumor regression, and mice simultaneously injected with Burkitt's cells and lymphoblastoid cells underwent tumor necrosis in most cases (11). In four separate experiments, the majority (12/21, 57%) of Burkitt's tumors developed extensive necrosis after local treatment with IP-10. The dose of IP-10 ranged between 200 and 400 ng/mouse/day (diluted in PBS containing 1% BSA) for 4 to 8 weeks. Superficial necrosis appeared after 22–49 days of IP-10 treatment. In contrast, control mice treated with buffer alone (PBS with 1% bovine serum albumin) did not develop tumor necrosis.

TABLE 3

Effects of IP-10 on Tumor-Induced Angiogenesis in vivo

| Exp. No. | Treatment | No. Mice Treated | Mean Tumor Size At Start of Treatment | No Mice With Tumor Necrosis/ Total Treated |
|---|---|---|---|---|
| 1 | None | 4 | N.A. | 0/4 |
|   | Buffer | 5 | 0.27 | 0/5 |
|   | LCL | 4 | N.A. | 3/4 |
|   | IP-10 | 9 | 0.25 | 5/9 |
| 2 | None | 2 | N.A. | 0/2 |
|   | Buffer | 2 | 0.25 | 0/2 |
|   | LCL | 3 | N.A. | 3/3 |
|   | IP-10 | 5 | 0.39 | 3/5 |
| 3 | Buffer | 2 | 0.39 | 0/2 |
|   | LCL | 1 | N.A. | 1/1 |
|   | IP-10 | 4 | 0.45 | 2/4 |
| 4 | Buffer | 2 | 0.35 | 0/2 |
|   | LCL | 1 | N.A. | 1/1 |
|   | IP-10 | 3 | 0.27 | 2/3 |

Sublethally irradiated (400 rad) BALB/c nu/nu female mice (1–9 condition) were injected subcutaneously with $10^6$ Burkitt's lymphoma cells (CA 46 cell line) either alone or mixed with $10^6$ Lymphoblastoid cells (LCL) from the cell line VDS. After the tumor reached a size of at least 0.25 cm$^2$, the mice injected with Burkitt's cell alone were injected intratumor daily with either buffer alone (PBS with 1% BSA, 0.1 ml) or with IP-10 at either 200 or 400 ng/mouse diluted in 0.1 ml PBS containing 1% BSA. The results reflect the evaluation of tumors 6 to 8 weeks after inoculation of the Burkitt's cells. Tumor necrosis is defined as positive if it involved at least 30% of the tumor mass, as determined after removal of the entire tumor, fixation, and staining of microscope sections with Hematoxilln Eosin.

Figure 3A:
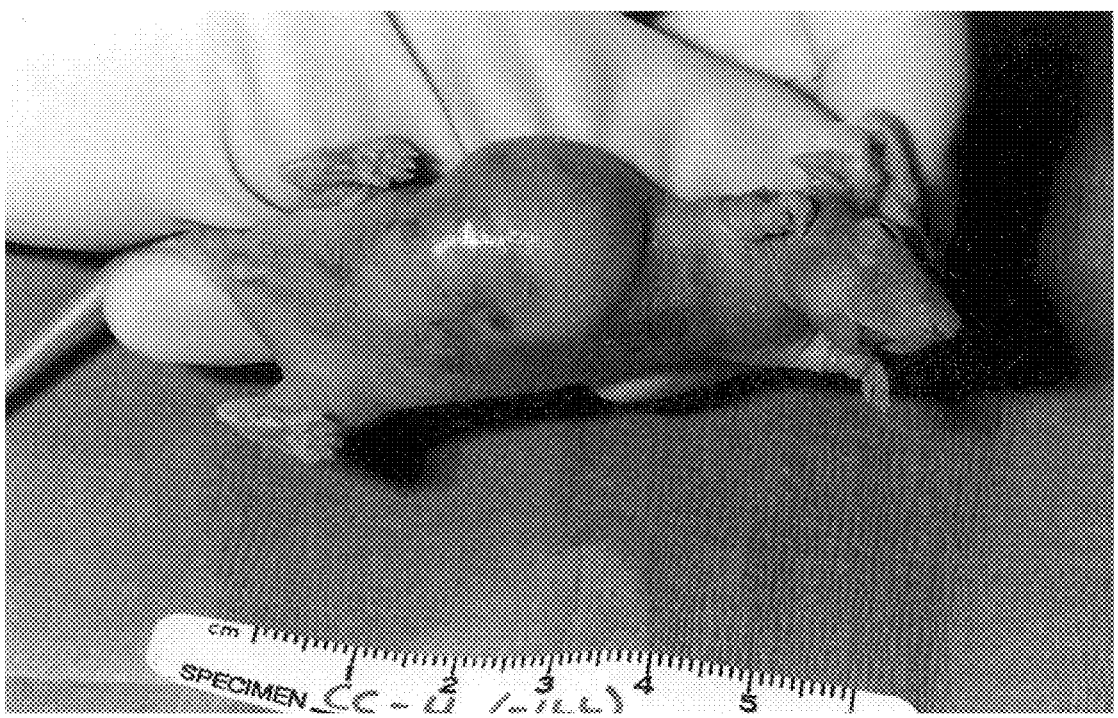
FIGS. 3A through 3B show photographs of representative athymic mice bearing Burkitt's tumors treated with either buffer alone (FIG. 3A) or with IP-10 (FIG. 3B).
Figure 3B:

Visual inspection of athymic mice bearing Burkitt's tumors either not treated or inoculated with control buffer showed large viable looking tumors 4–6 weeks after injection of the Burkitt's cells. In contrast, most mice treated with IP-10 showed macroscopic evidence of tumor necrosis at the same time points. FIGS. 3A and 3B show photographs of representative mice bearing Burkitt's tumors treated either with buffer alone (FIG. 3A) or with IP-10 (FIG. 3B). The occurrence of superficial extensive tumor necrosis is apparent in the IP-10 treated mouse but not in the control.

Figure 4A:
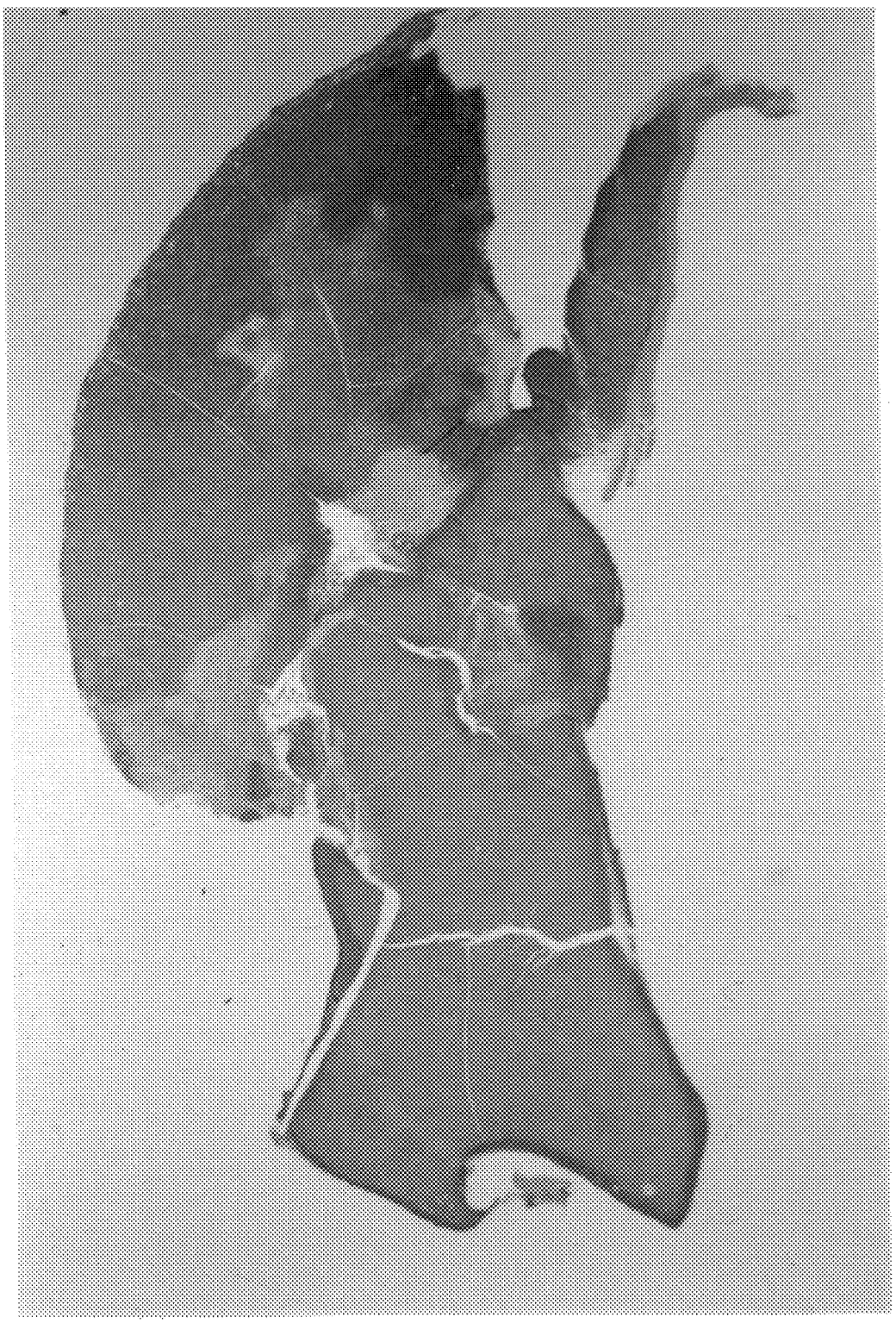
FIGS. 4A through 4B show photographs of representative tissue sections of Burkitt's tumors treated with buffer alone (FIG. 4A) or with IP-10 (FIG. 4B).
Figure 4B:

Visual examination of the tumor masses after removal from the animal, fixation and staining with hematoxylin eosin revealed marked differences depending upon whether the Burkitt's tumors had gone untreated (or treated with control buffer) and those treated with IP-10. As shown in representative sections (FIG. 4A and 4B), Burkitt's tumors that had received buffer alone appeared mostly viable throughout (FIG. 4A), but Burkitt's tumors treated with IP-10 showed large areas of necrosis extending widely and deeply within the tumor mass (FIG. 4B).

Figure 5A:
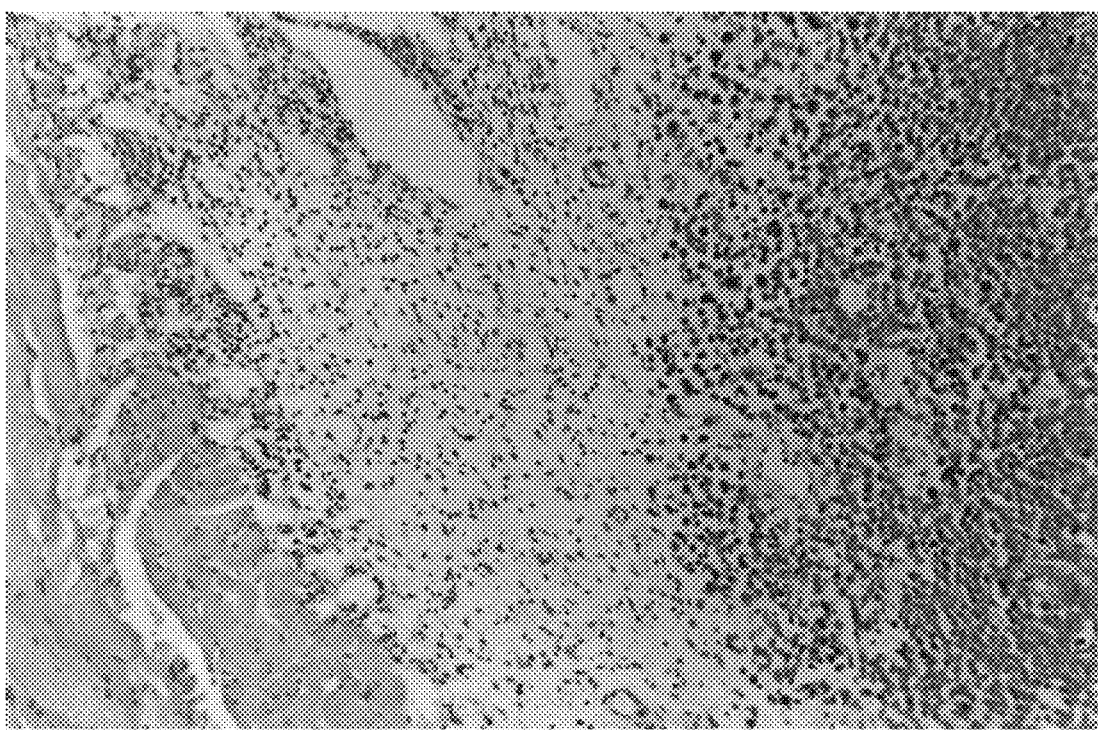
FIGS. 5A and 5B show representative micrographs of tissue sections from Burkitt's tumors treated with IP-10.
Figure 5B:
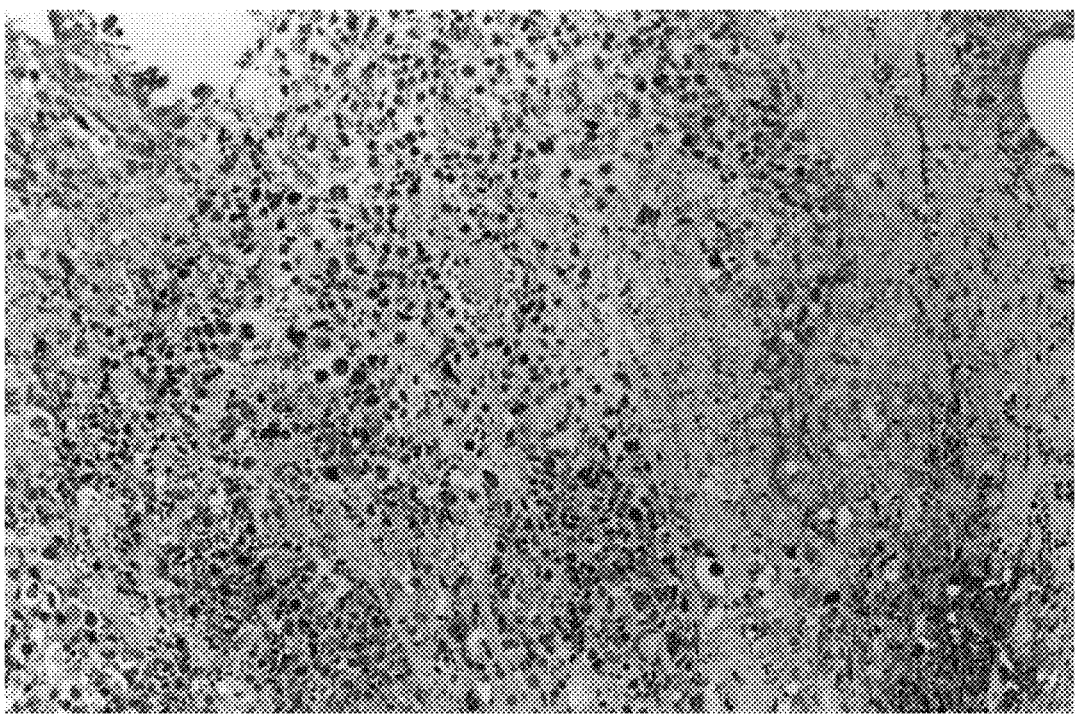

Microscopic examination of Burkitt's tumors treated with IP-10 showed in most cases massive central necrosis extending to the epidermis and deep into the tumor mass, surrounded by areas of viable tumor. Infiltration with monocytic cells was evident in areas separating live and dead tumor tissue, but lymphocyte infiltration was remarkably absent. Importantly, both the areas at the interface between live and dead tissue as well as areas of live tumor tissue has evidence of prominent endothelial cell damage, with thickening of the endothelial vessel wall and intravascular thrombosis (FIG. 5A and 5B).

These findings, combined with the in vitro and in vivo data presented above, document an antiangiogenic effect of IP-10 in vivo. The in vitro data showed that IP-10 inhibits endothelial cell differentiation into tubular structures that represent primordial capillaries and the in vivo data using the Matrigel assay show that IP-10 inhibits bFGF-induced neovascularization. The studies presented in the current example document that IP-10 inhibits neovascularization in vivo that is driven by a progressively growing tumor. It should be noted that all studies were performed in T cell immunodeficient animals, confirming that IP-10 does not require T cells and/or T cell functions to act as an antiangiogenic compound. Furthermore, the present model demonstrates that the antiangiogenic effect of IP-10 can be exploited for the treatment of malignancies arising in the context of severe T cell immunodeficiency.

The athymic mouse model used here represents a very useful animal model to study human malignancies and the treatment of human malignancies. The athymic mouse model has been successfully exploited and validated during the last two decades in the identification of efficacious therapeutics for treatment of human malignancies. Unlike non-immunocomprised animals, athymic mice allow for the growth of many human malignancies that would otherwise be rejected due to T cell immunity (11). In contrast to other mouse models where T cell immunodeficiency is combined

EXAMPLE 4
Method of Treating Kaposi's Sarcoma Using IP-10

Kaposi Sarcoma (KS) is an angioproliferative disease that is rare and mild in elderly men of Mediterranean origin, but is frequent and aggressive in association with AIDS. Both forms of KS, however, are characterized by similar macroscopic appearance and similar histology, including the presence of spindle shaped cells considered to be the tumor cells of KS in association with inflammatory cells and edema.

An experimental athymic mouse model was recently developed in which subcutaneous injection of $3 \times 10^6$ spindle cells of endothelial origin derived from KS lesions of AIDS patients (AIDS KS cells) gives rise to subcutaneous lesions that are characteristic of early stage Kaposi sarcoma 6–7 days after inoculation (31). Similar lesions are also induced 6–7 days after subcutaneous inoculation of 30–90 micrograms of recombinant bFGF (Boehringer-Manheim) into athymic mice. Groups of 20 athymic BALB/c nu/nu mice (female 4–8 weeks old) are injected with either AIDS KS cells alone ($3 \times 10^6$ cells, suspended in 100 microliters PBS containing 1% BSA), bFGF alone (Boerhinger-Manheim, 50 micrograms diluted in PBS containing 1% BSA) or buffer alone (100 microliters PBS containing 1% BSA). Twenty four hours following inoculation, one half of the mice in each group are inoculated with IP-10 (400 ng/mouse in 100 microliter of PBS containing 1% BSA) or control buffer alone (100 microliters PBS containing 1% BSA). This treatment is repeated daily for one week. When treatment is completed, mice are killed, tissue samples are fixed in formalin, and analyzed microscopically after hematoxylin-eosin staining. The effects of IP-10 are evaluated by comparison with the controls, and graded according to the intensity of blood vessel formation, spindle cells proliferation, neutrophil and mononuclear inflammatory cell infiltration and edema, with values ranging from 1–7, as previously described (31). In additional experiments, both the concentration of IP-10 are varied to include lower (10 ng) and higher concentrations (1 microgram), as well as the dosing (every day vs twice/day every other day), and the route of administration (s.c. vs. i.v., vs. i.p.).

In addition, IP-l0 is injected into Kaposi's sarcoma lesions to determine if IP-10 reduces the size of the lesion and/or delays disease progression. To this end, a phase 1 clinical study is initiated in which cohorts of HIV-infected patients with measurable skin lesions diagnosed as Kaposi's sarcoma will receive intralesional injections of IP-10. The starting dose of IP-10 is 100 ng delivered in 100–200 microliters of an appropriate formulation buffer (for example PBS containing 1% human serum albumin). Intralesional injections at this dose will be repeated daily in individual patients for 30 days. If little/no toxicity is observed, another cohort of patients receive IP-10 at 200 ng/dose by the same route. Subsequent patient cohorts receive IP-10 at doses increased by a factor of 2, until toxicity attributable to IP-10 is observed. All patients are followed for general symptoms and appropriate laboratory parameters. At weekly intervals, the Kaposi's lesions are measured for size, counted, and their nodularity, i.e. the extent to which they are raised, are evaluated by standard techniques known in the art.

The phase I, toxicity study, identifies a maximum tolerated dose of IP-10 and may provide some information regarding the efficacy of IP-10 as a biological therapeutic for Kaposi's sarcoma. Subsequent phase II studies are designed to determine the efficacy of IP-10 in this setting and explore various parameters, including but not limited to, regimens, doses, routes of administration, excipients and combination therapies.

EXAMPLE 5
Method of Treating Diabetic Retinopathy Using IP-10

Diabetic retinopathy is believed to occur in response to local production of an angiogenic diffusible factor that is presumably induced in response to retinal ischemia. As a consequence of local production of an angiogenic factor, neovascularization of the retina, optic nerve or iris occur. Suppression of angiogenesis is believed to be important to prevent or delay disease progression. Initially, IP-10 is tested for efficacy in preclinical models that closely mimic various aspects of diabetic retinopathy.

A. One experimental model utilizes the chick embryo choliocallantoic membrane (CAM) assay (25). This assay has been extensively used for the detection of inhibition of angiogenesis (32). Fertilized 3-day old white Leghorn eggs (Spafas, Norwich, Conn.) are cracked, and embryos with intact yolks are placed in 100 mm×20 mm Petri dishes. After 3 days of incubation (37° C. in 3% $CO_2$), a methylcellulose (Fisher Scientific, Fair Lawn, N.J.) disc containing IP-10, analogs, derivatives, fragments, chimeric IP-10 or IP-10-PEG is applied to the CAM of individual embryos. The discs are prepared by desiccation of 10 microliter of 0.45% methycellulose (in water), with or without IP-10, on Teflon rods, as described (25). After 48 hr incubation, embryos and CAMs are observed by means of a stereomicroscope, and induction of avascular zones is measured. Concentrations of IP-10 ranging between 10 ng and 100 micrograms/embryo are evaluated in groups of 10–15 embryos each.

B. Another experimental model utilizes implantation of a sustained release pellet containing appropriate amounts of an angiogenic factor, such as 80 ng basic fibroblast growth factor, into a corneal pocket of mice, as described by Muthukkaruppan and Auerbach, 1979 (33). As a consequence of local release of the angiogenic factor, growth of capillary vessels is observed from the corneal limbus, across the cornea, and reaching into the pellet within 6 days. IP-10, analogs, derivatives, fragments, chimeric IP-10 or IP-10-PEG is administered systemically to groups of mice that have received the bFGF-containing pellet and a reduction/abrogation of corneal angiogenesis is determined. Administration of IP-10 includes the i.v., i.p., and s.c. routes. The starting dose consists of 1 microgram/mouse and is repeated every day beginning on the day of pellet implantation and continued for 1 week. The dose is escalated by a factor of 5 in subsequent cohorts of mice. IP-10 may also be administered continuously using a slow release pump containing IP-10 to be placed subcutaneously in order to maintain a constant concentration of biologically active IP-10.

C. Another experimental model system utilizes cynomologous monkeys (34,35). Retinal ischemia is first induced by laser (Coherent Lambda Plus, Palo Alto, Calif.) occlusion of all branch retinal veins. Fundus photography and fluorescein angiography, using 0.1 cc/kg of 10% sodium fluorescein via saphenous vein is used to verify the occurrence of vein occlusion. Local ischemia is known to induce increased production of the angiogenic factor, vascular endothelial growth factor (VEGF) that can be measured in the aqueous fluid. Subsequently, iris neovascularization is observed and measured. A standardized grading system for iris neovascularization in this model has been developed (35) using standard photographs and angiograms. This system analyses the vessel density and the degree of fluorescein leakage. Briefly, grade 0 reflects a normal iris, with few vessels and no leakage. Grade 1 has an increased vascular pattern without leakage and is typical of regressed neovascularization. Grades 2 and 3 identify increasing levels of vessel density and degrees and rapidity of fluorescein leakage. Grade 4 identified enough neovascular tissue to render the iris opaque within the first 35 seconds of the angiogram. Grade 5 has the characteristics of grade 4 plus ectropion uvea or glaucoma. Using this animal model and the grading system outlined above, the effects of IP-10 in reducing the neovascularization process induced by occlusion of all retinal veins is evaluated. To this end monkeys that have already been subjected to retinal vein occlusion are inoculated systemically (i.v., s.c., or i.m.) with doses of IP-10, analogs, derivatives, fragments, chimeric IP-10, or IP-10-PEG ranging between 10 micrograms/animal/day for 7–10 days to 100 micrograms/animal/day. The effect of IP-10 treatment on ocular neovascularization is evaluated. In addition, monkeys are observed and monitored for evidence of any IP-10 toxicities.

EXAMPLE 6
Method of Regulating Wound Healing Using IP-10

Pathological angiogenesis is characterized by the persistent proliferation of endothelial cells, and is a prominent feature of diseases such as, but not limited to, rheumatoid arthritis, scleroderma, lupus erythematosus, and psoriasis. Although controlled angiogenesis occurs during a variety of physiological processes, such as embryogenesis and wound repair, wound healing can be associated with excessive neovascularization and may result in keloid formation, excessive dermal scarring, and other complications. Thus, it may appropriate in a number of circumstances to inhibit physiological neovascularization to prevent or alleviate complications of excessive neovascularization.

The utility of IP-10 as an inhibitor of neovascularization associated with wound healing is tested in the ischemic rabbit ear dermal ulcer model (36). New Zealand white rabbits (weight between 2.7 and 3.2 kg) are used in these experiments. Wounds are made (no. 4), the center of which is located 4 cm. proximal to the tip of the ear. Using a 6-mm surgical punch biopsy instrument, wounds are made down to the bare cartilage with the aid of the operating microscope to insure uniformity and precision. The wounds are immediately covered with polyurethane film (Tegaderm, 3M, Minneapolis, Minn.) to prevent drying. One ear serves as a control and the other is subjected to surgery to reduce blood supply. The rabbits are first anesthetized and then subjected to surgery to selectively reduce blood supply to the ear by occlusion of the rostral and central arteries, with preservation of the caudal artery and all three veins. This surgical procedure causes the ear to become pale and cool without significant edema until day 7, and blood flow measurements indicate a significant reduction on postoperative days 1, 3 and 7. In this experimental system, wound repair occurs almost entirely by neovascularization and formation of new tissue, rather than by wound contraction that is limited to less than 3%. IP-10 is injected systemically (i.v., i.m., s.c.) into New Zealand rabbits and follow healing of ear wounds generated as described above. The dose of IP-10, analogs, derivatives, fragments, chimeric IP-10 or IP-10 PEG ranges between 1–50 micrograms/animal/day. The effects of IP-10 is scored in terms epithelialization, granulation tissue formation and presence of tissue necrosis.

EXAMPLE 7
Anti-Angiogenic Effect of the Combination Therapy of Interferon-Inducible Protein 10 Plus Angiostatin As previously demonstrated in Example 2, IP-10 inhibits neovascularization in vivo, as measured in the matrigel assay conducted in athymic mice. O'Reilly et al (25) have demonstrated that Angiostatin inhibits neovasculatization in vivo, as detected in the mouse corneal micropocket assay and in the chick embryo chorioallantoic membrane (CAM) assay. As mentioned above, Angiostatin inhibits endothelial cell proliferation induced by bFGF and this is presumably its mechanism of action. In contrast, IP-10 inhibits endothelial cell differentiation into tubular structures without inhibiting endothelial cell proliferation. Presumably, IP-10 inhibits neovascularization by inhibiting endothelial cell differentiation. Thus, Angiostatin and IP-10 individually inhibit angiogenesis through distinct pathways. It is therefore likely that their effects on angiogenesis are additive and more likely synergistic.

Initially, the in vivo Matrigel assay (15) is employed. Groups of 10 BALB/c nu/nu mice are injected subcutaneously with either Matrigel alone (0.5 ml); Matrigel (0.5 ml) plus bFGF (150 ng/ml); Matrigel (0.5 ml) plus bFGF (150 ng/ml) plus IP-10 (400 ng/ml); Matrigel (0.5 ml) plus bFGF (150 ng/ml) plus Angiostatin (400 ng/ml); and Matrigel (0.5 ml) plus bFGF (150 ng/ml) plus IP-10 (400 ng/ml) plus Angiostatin (400 ng/ml). In addition the concentration of IP-10 is varied to include the range 1–400 ng/ml and those of Angiostatin to include the range of 1–400 ng/ml used both individually and together in the in vivo Matrigel assay. This experiment reveals a) whether Angiostatin is antiangiogenic in this assay; b) whether the combination of IP-10 and Angiostatin act additively or synergistically in inhibiting angiogenesis; and c) the optimal dose of each compound to achieve maximal inhibition.

The in vivo mouse corneal micropocket assay, described above (25) is also used to determine the combined anti-angiogenic effects of IP-10 plus angiostatin. A corneal pocket is created with a cataract knife in the eye of an 8 to 10 week old male C57BL6/J mouse. Into this pocket, a 0.34 mm×0.34 mm sucrose aluminum sulfate (Bukh Meditec, Copenhagen, Denmark) pellet coated with hydron polymer type NCC (Interferon Sciences, New Brunswick, N.J.) containing 80–100 ng of bFGF is implanted. The pellet is positioned 1–1.5 mm from the corneal limbus. Immediately after pellets are implanted the mice are treated with either buffer alone, IP-10 alone, Angiostatin alone, or a combination of Angiostatin and IP-10. Initially, s.c. daily inoculations of IP-10 at 10 micrograms/mouse and of Angiostatin at 10 micrograms/mouse are employed. Subsequently, the dose of each IP-10 and Angiostatin alone or in combination are varied to cover the ranges of 1 to 100 micrograms/mouse day. Other routes of administration, i.v. and i.p. are tested.

The combined effects of IP-10 and Angiostatin on tumor-induced angiogenesis is also studied. Initially, the Burkitt's lymphoma nude mouse model described above (11) is utilized. When injected subcutaneously into athymic mice, Burkitt's lymphoma cells generally give rise to progressively growing tumors that induce neovascularization to support tumor growth. As described above, IP-10 injected into established Burkitt's tumors causes tumor necrosis in the majority of animals. In this experiment the combined effect of IP-10 and Angiostatin in reducing tumor-induced angiogenesis is determined. To this end, sublethally irradiated athymic BABL/c nu/nu mice (4–8 weeks old) are injected subcutaneously with $10^6$ human Burkitt's lymphoma cells. After the subcutaneous tumors reach 0.25 $cm^2$ in surface area, some mice are injected with buffer alone, other with IP-10 alone, other with Angiostatin alone, and others with IP-10 and Angiostatin combined. Initially, IP-10 and Angiostatin are injected intratumor at 400 ng/mouse/day for 6–8 weeks, a regimen proved effective for IP-10 alone. Subsequently, the doses of IP-10 and Angiostatin are varied to cover the range of 0.1 to 10 micrograms/mouse/day, when used individually and together. This experiment determines the effects of combination therapy of IP-10 and Angiostatin in reducing tumor induced angiogenesis and secondary tumor necrosis and tumor regression.

REFERENCES

1. Folkman, J., and Y. Shing. 1992. Angiogenesis. *J. Biol. Chem.* 267, No. 16:10931–10934.

2. Folkman, J. 1992. The Role of Angiogenesis in Tumor Growth. *Cancer Biology.* 3:65–71.

3. Muller, G., J. Behrens, U. Nussbaumer, P. Bohlen, and W. Birchmeier. 1987. Inhibitory Action of Transforming Growth Factor β on Endothelial Cells. *Proc. Natl. Acad. Sci.* 84:5600–5604.

4. Good, D. J., Polverini, F. Rastinejad, M. M. LeBeau, R. S. Lemons, W. A. Frazier, and N. P. Bouck. 1990. A Tumor Suppressor-dependent Inhibitor of Angiogenesis is Immunologically and Functionally Indistinguishable From a Fragment of Thrombospondin. *Proc. Natl. Acad. Sci.* 87:6624–6628.

5. Cozzolino, F., M. Torcia, D. Aldinucci, M. Ziche, F. Almerigogna, D. Bani, and D. Stern. 1990. Interleukin 1 is an autocrine Regulator of Human Endothelial Cell Growth. *Proc. Natl. Acad. Sci.* 87:6487–6491.

6. Friesel, R., A. Komoriya, and T. Maciag. 1987. Inhibition of Endothelial Cell Proliferation by γ-Interferon. *J. Cell. Biol.* 104:689–696.

7. Takigawa, M., Y. Nishida, F. Suzuki, J. Kishi, K. Yamashita, and T. Hayakawa. 1990. Induction of Angiogenesis in Chick Yolk-Sac Membrane by Polyamines and its inhibition by Tissue Inhibitors of Metalloproteinases (TIMP and TIMP-2). *Biochem. Biophy. Res. Commun.* 171:1264–1271.

8. Maione, T., G. Gray, L. Petro, A. Hunt, A. Donner, S. Bauer, H. Carson, and R. Sharpe. 1990. Inhibition of Angiogenesis by Recombinant Human Platelet Factor-4 and Related Peptides. *Science (Wash. DC)* 247:77–79.

9. Taylor, S., and J. Folkman. 1982. Protamine is an Inhibitor of Angiogenesis. *Nature (Lond.)* 297:307–312.

10. Ingber, D., T. Fujita, S. Kishimoto, K. Sudo, T. Kanamaru, H. Brem, and J. Folkman. 1990. Synthetic Analogues of Fumagillin That Inhibit Angiogenesis and Suppress Tumor Growth. *Nature (Lond.).* 348:555–557.

11. Tosato, G., C. Sgadari, K. Taga, K. Jones, S. Pike, A. Rosenberg, J. Sechler, I. Magrath, L. Love, and K. Bhatia. 1994. Regression of Experimental Burkitt's Lymphoma Induced by Epstein Barr Virus-Immortalized Human B Cells. *Blood.* 83:776–784.

12. Kleinman, H., M. McGarvey, J. Hassell, V. Star, F. Cannon, G. Laurie, and G. Martin. 1986. Basement Membrane Complexes with Biological Activity. *Biochemistry.* 25:312–318.

13. Garlanda, C., C. Parravicini, M. Sironi, M. DeRossi, R. Wainstok de Calmanovici, F. Carozzi, F. Bussolino, F. Colotta, A. Mantovani, and A. Vecchi. 1994. Progressive Growth in Immunodeficient Mice and Host Cell Recruitment by Mouse Endothelial Cells Transformed by Polyoma Middle-sized T Antigen: Implications for the Pathogenesis of Opportunistic Vascular Tumors. *Proc. Natl. Acad. Sci.* 91:7291–7295.

14. Chopra, H., S. Filigiel, J. Hatfield, K. Nelson, C. Diglio, J. Taylor, and K. Honn. 1990. An In Vivo Study of the Role of the Tumor Cell Cytoskeleton in Tumor Cell-platelet-Endothelial Cell Interactions. *Cancer Res.* 50:7686–7696.

15. Passaniti, A., R. Taylor, R. Pili, Y. Guo, P. Long, J. Haney, R. Pauly, D. Grant, and G. Martin. 1992. A Simple, Quantitative Method for Assessing Angiogenesis and Antiangiogenic Agents Using Reconstituted Basement Membrane, Heparin, and Fibroblast Growth Factor. *Methods in Laboratory Investigation.* 67:519–528.

16. Grant, D., K. Tashiro, B. Segui-Real, Y. Yamada, G. Martin, and H. Kleinman. 1989. Two Different Laminin Domains Mediate the Differentiation of Human Endothelial Cells into Capillary-like Structures In Vitro. *Cell.* 58:933–943.

17. Pepper, M., A. Sappino, R. Montesano, L. Orci, and J. Vassalli. 1992. Plasminogen Activator Inhibitor-1 is Induced in Migrating Endothelial Cells. *J. Cell. Physiol.* 153:129–139.

18. Cid, M., D. Grant, G. Hoffman, R. Auerbach, A. Fauci, and H. Kleinman. 1993. Identification of Haptoglobin as an Angiogenic Factor in Sera from patients with Systemic Vasculitis. *J. Clin. Invest.* 91:977–985.

19. Luster, A., J. Unkeless, and J. Ravetch. 1985. γ-Interferon Transcriptionally Regulates an Early-Response Gene Containing Homology to Platelet Proteins. *Nature (Lond.)* 315:672–676.

20. Luster, A., and J. Ravetch. 1987. Biochemical Characterization of a γ Interferon inducible cytokine (IP-10). *J. Exp. Med.* 166:1084–1097.

21. Vanguri, P., and J. Farber. 1990. Identification of CRG-2 an Interferon-inducible mRNA Predicted to Encode a Murine Monokine. *Journal of Biological Chemistry.* 265:15049–15057.

22. Sarris, A., H. Broxmeyer, U. Wirthmueller, N. Karasavvas, S. Cooper, L. Lu, J. Krueger, and J. Ravetch. 1993. Human Interferon-Inducible Protein 10: Expression and Purification of Recombination Protein Demonstrate Inhibition of Early Human Hematopoietic Progenitors. *J. Exp. Med.* 178:1127–1132.

23. Luster, A., and P. Leder. 1993. IP-10, a C-X-C Chemokine, Elicits a Potent Thymus-dependent Antitumor Response In Vivo. *J. Exp. Med.* 178:1057–1065.

24. Taub, D. D., R. L. Loyd, K. Conlon, J. M. Wang, J. R. Ortaldo, A. Harada, K. Matsushima, D. J. Kelvin, and J. J. Oppenheim. 1993. Recombinant Human Interferon Inducible Protein 10 is a Chemoattractant for Human Monocytes and T lymphocytes and Promotes T cell Adhesion to Endothelial Cells. *J. Exp. Med.* 177:1809–1814.

25. O'Reilly, M. L., Holmgren, Y. Sing, C. Chen, R. Rosenthal, M. Moses, W. Lane, Y. Cao, H. Sige, and J. Folkman. Cell. 1984. Angiostatin, a Novel Angiogenesis Inhibitor that Mediates the Suppression of Metastases by Lewis Lung Carcinoma. *Cell.* 79:185–188.

26. Ezekowitz, A., J. Mulliken, and J. Folkman. 1992. Interferon alpha-2a Therapy for Life-threatening Hemangiomas of Infancy. *N. Engl. J. Med.* 326:1456–1463.

27. Koch, A., P. Polverini, S. Kunkel, L. Harlow, L. DiPetro, V. Elner, S. Elner, and R. Strieter. 1992. Interleukin-8 as a Macrophage-Derived Mediator of Angiogenesis. *Science (Wash. D.C.).* 258:1798–1801.

28. Smith, D. R., P. J. Polverini, S. L. Kunkel, M. B. Orringer, R. I. Whyte, M. D. Burdick, C. A. Wilke, and R.

M. Strieter. 1994. Inhibition of Interleukin 8 Attenuates Angiogenesis in Bronchogenic Carcinoma. *J. Exp. Med.* 179:1409–1415.

29. Baggiolini, M., and C. Dahinden. 1994. CC Chemokines in Allergic Inflammation. *Immunol. Today.* 15:127–133.

30. J. M. Farber. 1993. HuMig: A New Human Member of the Chemokine Family of Cytokines. *Biochem. Biophy. Res. Commun.* 192:223–230.

31. Ensoli, B. Gendelman, R., Markham, P., Fiorelli, V., Colombini S., Raffeld, M., Cafaro A., Chang H-K, Brady J. N. and Gallo R. 1994. Synergy between basic fibroblast growth factor and HIV-1 Tat protein in induction of Kaposi's sarcoma. *Nature* 371:674–680.

32. Nguyen M. Shing Y., and Folkman J. 1994. Quantitation of angiogenesis in the chick embryo chorioallantoic membrane, *Microvascular Res.* 47:31–40.

33. Muthukkaruppan V., and Auerbach R., 1979. Angiogenesis in the mouse cornea. *Science* 28 1416–1418.

34. Virdl P. S. and Hayreh S S. 1982. Ocular neovascularization with retinal vascular occlusion. I. Association with experimental retinal vein occlusion. *Arch. Opthalmol.* 100:331–341.

35. Miller J. W., Adamis A. P. Shima D. T., D'Amore P. A., Moulton R. S., O'Reilly, Folkman J., Dvorak H. F., Brown L. F., Berse B., Yeo T-K and Yeo K-T. Vascular endothelial growth factor/vascular permeability factor is temporally and spatially correlated with ocular angiogenesis in a primate model. *Amer J Pathol* 145: 574–584.

36. Ahn S A, and Mustoe T A. 1990. Effects of ischemia on ulcer wound healing: a new model in the rabbit ear. *Ann. Plast. Surg.* 24:17–23.

We claim:

1. An anti-angiogenic polypeptide having at least 10 contiguous amino acids selected front the amino acid sequence interferon-inducible protein 10, said polypeptide having a length in the range of 10 amino acids to less than 35 amino acids, excluding a polypeptide consisting of amino acid sequence SEQ. ID No.: 18 and excluding a polypeptide consisting of amino acid residues 6 through 22 of SEQ. ID No.: 7.

2. The anti-angiogenic polypeptide according to claim 1, wherein said polypeptide has less than 25 amino acids, excluding a polypeptide consisting of amino acid sequence SEQ. ID No.: 18 and excluding a polypeptide consisting of amino acid residues 6 through 22 of SEQ ID No.: 7.

3. An anti-angiogenic polypeptide having at least 10 contiguous amino acids selected from the amino acid sequence interferon-inducible protein 10, wherein said polypeptide has a length of 10 to 15 amino acids.

4. The anti-angiogenic polypeptide according to claim 1, wherein said polypeptide is selected from the group consisting of SEQ. ID No.: 1, SEQ. ID No.: 2, SEQ. ID No.: 3, SEQ. ID No.: 4, SEQ. ID No.: 5, SEQ. ID No.: 6, SEQ. ID No. 7, SEQ. ID No.: 8, SEQ. ID No.: 9, SEQ. ID No.: 10, SEQ. ID No.: 11, SEQ. ID No.: 12, SEQ. ID No.: 13, SEQ. ID No.: 14, SEQ. ID No.: 15, SEQ. ID No.: 16, SEQ. ID No.: 17, SEQ. ID No.: 19, SEQ. ID No.: 20, and SEQ. ID No.: 21.

5. A pharmaceutical composition capable of inhibiting angiogenesis comprising polypeptides of claims 1, 2, or 3 and further comprising an anti-inflammatory agent or further comprising an anti-inflammatory agent and a chemotherapeutic agent.

6. A pharmaceutical composition capable of inhibiting angiogenesis comprising interferon inducible protein 10 or fragment thereof, said fragment having at least 10 contiguous amino acids and further comprising an anti-inflammatory agent or further comprising an anti-inflammatory agent and a chemotherapeutic agent.

7. A pharmaceutical composition capable of inhibiting angiogenesis comprising an anti-angiogenic factor selected from the group consisting of SEQ. ID No.: 1, SEQ. ID No.: 2, SEQ. ID No.: 3, SEQ. ID No.: 4, SEQ. ID No.: 5, SEQ. ID No.: 6, SEQ. ID No.: 7, SEQ. ID No.: 8, SEQ. ID No.: 9, SEQ. ID No.: 10, SEQ. ID No.: 11, SEQ. ID No.: 12, SEQ. ID No.: 13, SEQ. ID No.: 14, SEQ. ID No.: 15, SEQ. ID No,: 16, SEQ. ID No.: 17, SEQ. ID No.: 19, SEQ. ID No.: 20, SEQ. ID No.: 21 and combinations thereof and a pharmaceutically acceptable carrier.

8. A pharmaceutical composition according to claim 7 further comprising an anti-inflammatory agent.

9. A pharmaceutical composition according to claim 8 wherein the anti-inflammatory agent is selected from the group consisting of ibuprofen, aspirin, prednisone, and mixtures thereof.

10. A pharmaceutical composition capable of inhibiting angiogenesis comprising a first anti-angiogenic factor selected from the group consisting of SEQ. ID No.: 1, SEQ. ID No.: 2, SEQ. ID No.: 3, SEQ. ID No.: 4, SEQ. ID No.: 5, SEQ. ID No.: 6, SEQ. ID No.: 7, SEQ. ID No.: 8, SEQ. ID No.: 9, SEQ. ID No.: 10, SEQ. ID No.: 11, SEQ. ID No.: 12, SEQ. ID No.: 13, SEQ. ID No.: 14, SEQ. ID No.: 15, SEQ. ID No.: 16, SEQ. ID No.: 17, SEQ. ID No.: 18, SEQ. ID No.: 19, SEQ. ID No.: 20, SEQ. ID No.: 21, and combinations thereof; and a second anti-angiogenic factor, and a pharmaceutically acceptable carrier, wherein the second anti-angiogenic factor is selected from the group consisting of angiostatin, PF4, IFN-α, fumagillin, AGM-1470, thrombospondin and mixtures thereof.

11. A pharmaceutical composition capable of inhibiting angiogenesis comprising interferon inducible protein 10 or fragments thereof, said fragment having at least 10 contiguous amino acids and further comprising an anti-inflammatory agent, or further comprising an anti-inflammatory agent and a chemotherapeutic agent, wherein the anti-inflammatory agent is selected from the group consisting of ibuprofen, aspirin, prednisone and mixtures thereof.

12. A method of inhibiting angiogenesis at a site in a mammal having an angiogenic disease other than cancer comprising administration of an effective amount of interferon-inducible protein 10 or fragments thereof, said fragments having at least 10 contiguous amino acids, said amount is sufficient to inhibit angiogenesis at the site.

13. A method of inhibiting an inducer of angiogenesis at a site in a mammal having an angiogenic disease other than cancer comprising administration of an effective amount of interferon-inducible protein 10 or fragment thereof, said fragment having at least 10 contiguous amino acids, said amount is sufficient to inhibit the inducer of angiogenesis at the site.

14. A method of inhibiting endothelial cells from differentiating into tubular capillary structures at a site other than a cancer site comprising exposure of the endothelial cells to an effective amount of interferon inducible protein 10, or fragment thereof, said fragment having at least 10 contiguous amino acids, said amount inhibits differentiation of the endothelial cells.

15. A method of inhibiting angiogenesis at a tumor site in an immunocompromised mammal comprising administration of an effective amount of an anti-angiogenic factor selected from the group consisting of SEQ. ID No.:1, SEQ. ID No.: 2, SEQ. ID No.: 3, SEQ. ID No.: 4, SEQ. ID No.: 5, SEQ. ID No.: 6, SEQ. ID No.: 7, SEQ. ID No.: 8, SEQ. ID No.: 9, SEQ. ID No.: 10, SEQ. ID No.: 11, SEQ. ID. No.: 12, SEQ. ID No.: 13, SEQ. ID No.: 14, SEQ. ID No.: 15, SEQ. ID No.: 16, SEQ. ID No.: 17, SEQ. ID No.: 18, SEQ. ID No.: 19, SEQ. ID No.: 20, SEQ. ID No.: 21, and combinations thereof; said amount is sufficient to inhibit angiogenesis at the tumor site in the immunocompromised mammal, wherein said immunocompromised mammal is immunicompromised due to a T lymphocyte deficiency or a T lymphocyte depletion.

16. A method of inhibiting angiogenesis at a site in a mammal having an angiogenic disease comprising administration of an interferon-inducible protein 10 fragment, wherein the fragment is selected from the group consisting of SEQ. ID No.: 1, SEQ. ID No.: 2, SEQ. ID No.: 3, SEQ. ID No.: 4, SEQ. ID No.: 5, SEQ. ID No.: 6, SEQ. ID No.: 7, SEQ. ID No.: 8, SEQ. ID No.: 9, SEQ. ID No.: 10, SEQ. ID No.: 11, SEQ. ID No.: 12, SEQ. ID No.: 13, SEQ. ID No.: 14, SEQ. ID No.: 15, SEQ. ID No.: 16, SEQ. ID No.: 17, SEQ. ID No.: 18, SEQ. ID No.: 19, SEQ. ID No.: 20, SEQ. ID No.: 21, and combinations thereof; and a second anti-angiogenic factor, and a pharmaceutically acceptable carrier.

17. A method of inhibiting angiogenesis at a site in a mammal having an angiogenic disease, said angiogenic disease selected from the group consisting of diabetic retinopathy, retrolental fibroplasia, trachoma, neovascular glaucoma, psoriases, immune-inflammation, non-immune inflammation, atherosclerosis, and excessive wound repair, comprising administration of an effective amount of interferon-inducible protein 10 or fragment thereof, said fragment having at least 10 contiguous amino acids, said amount is sufficient to inhibit angiogenesis at the site.

18. A method of inhibiting angiogenesis at a site in a mammal having an angiogenic disease, said angiogenic disease consisting of immune inflammation wherein the immune inflammation is caused by an autoimmune disease selected from the group consisting of rheumatoid arthritis, systemic lupus erythematosus, thyroiditis, Goodpasture's syndrome, systemic vasculitis, scleroderma, Sjogren's syndrome, sarcoidosis, and primary biliary cirrhosis and said method comprising administration of an effective amount of interferon-inducible protein 10 or fragment thereof, said fragment having at least 10 continuous amino acids, said amount is sufficient to inhibit angiogenesis at the site.

19. A method of inhibiting angiogenesis according to claim 12, wherein the mammal is immunocompromised due to a T lymphocyte deficiency or a T lymphocyte depletion.

20. A method of inhibiting angiogenesis according to claim 12 wherein the site is a dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle, or respiratory tract.

21. A method according to claim 13 wherein the inducer of angiogenesis is selected from the group consisting of basic fibroblast growth factor, acidic fibroblast growth factor, hepatocyte growth factor, IL-8 and vascular endothelial growth factor.

22. A method according to claim 13 wherein the site is a dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle or respiratory tract.

23. A method according to claim 13 further comprising administration of an effective amount of a second anti-angiogenic agent.

24. A method according to claim 14 wherein the endothelial cell is selected from the group consisting of a pulmonary endothelial cell, a heart endothelial cell, gastrointestinal endothelial cell, a brain endothelial cell, a lymphatic endothelial cell, a genital-urinary endothelial cell, a skin endothelial cell, a bone endothelial cell, a muscle endothelial cell, a breast endothelial cell, a retinal endothelial cell, an endocrine endothelial cell, a central nervous system endothelial cell, a hepatic endothelial cell, and an umbilical cord endothelial cell.

25. A method of inhibiting angiogenesis according to claim 15, wherein the tumor site is at a Kaposi's sarcoma.

26. The method of inhibiting angiogenesis at a tumor site according to claim 15, wherein the T lymphocyte deficiency or T lymphocyte depletion is congenital or acquired.

27. A method of inhibiting angiogenesis according to claim 12 or 15 wherein a route of administration is intravenously, intramuscular, intrathecal, intradermal, intraperitoneal, subcutaneous, intrapleural, intrauterine, rectal, vaginal, topical, intratumor, transdermal, or transmucosal.

28. A method of inhibiting angiogenesis according to claim 12 or 15 wherein a dose of at least 0.1 mg/kg is administered.

29. A method of inhibiting angiogenesis according to claim 12 or 15 wherein a dose of at least 25 mg/kg is administered.

30. A method of inhibiting angiogenesis according to claim 12 or 15 wherein a dose of about 1 mg/kg to about 100 mg/kg is administered.

31. A method of inhibiting angiogenesis at a tumor site according to claim 15 wherein the mammal is immunocompromised by a genetic defect, an autoimmune disease, immunosuppressive agents, chemotherapeutic agents, radiation therapy, cancer or a viral infection.

32. A method according to claim 15 wherein the site is a dermis, epidermis, endometrium, retina, surgical wound, gastrointestinal tract, umbilical cord, liver, kidney, reproductive system, lymphoid system, central nervous system, breast tissue, urinary tract, circulatory system, bone, muscle or respiratory tract.

33. A method of inhibiting angiogenesis at a tumor site in an immunocompromised mammal according to claim 15 further comprising administration of an effective amount of a second anti-angiogenic agent.

34. The method according to claim 33 wherein the second anti-angiogenic agent is selected from the group consisting of angiostatin, platelet factor 4, interferon-α, fumagillin, AGM-1470, thrombospondin and mixtures thereof.

35. The method according to claim 15 further comprising administration of an effective amount of a chemotherapeutic agent.

* * * * *